US012653821B2

(12) United States Patent
Ying et al.

(10) Patent No.: US 12,653,821 B2
(45) Date of Patent: *Jun. 16, 2026

(54) CARIPRAZINE PHARMACEUTICAL COMPOSITION, PREPARATION METHOD AND APPLICATION THEREOF

(71) Applicant: SHANGHAI BOCIMED PHARMACEUTICAL CO., LTD., Shanghai (CN)

(72) Inventors: Shuhuan Ying, Shanghai (CN); Zhixiang Chen, Shanghai (CN); Xian Zhang, Shanghai (CN); Tao Zhu, Shanghai (CN); Tingting Wang, Shanghai (CN)

(73) Assignee: SHANGHAI BOCIMED PHARMACEUTICAL CO., LTD., Shanghai (CN)

( * ) Notice: Subject to any disclaimer, the term of this patent is extended or adjusted under 35 U.S.C. 154(b) by 472 days.

This patent is subject to a terminal disclaimer.

(21) Appl. No.: 18/043,201

(22) PCT Filed: Aug. 26, 2021

(86) PCT No.: PCT/CN2021/114754

§ 371 (c)(1),
(2) Date: Feb. 27, 2023

(87) PCT Pub. No.: WO2022/042642

PCT Pub. Date: Mar. 3, 2022

(65) Prior Publication Data

US 2023/0414504 A1 Dec. 28, 2023

(30) Foreign Application Priority Data

Aug. 26, 2020 (CN) ........................ 202010869671.7
Aug. 26, 2020 (CN) ........................ 202010870701.6
Mar. 26, 2021 (CN) ........................ 202110324874.2
Mar. 26, 2021 (CN) ........................ 202110330670.X

(51) Int. Cl.

*A61K 31/495* (2006.01)
*A61K 9/00* (2006.01)
*A61K 47/02* (2006.01)
*A61K 47/26* (2006.01)
*A61K 47/38* (2006.01)
*A61K 9/10* (2006.01)

(52) U.S. Cl.

CPC .......... *A61K 31/495* (2013.01); *A61K 9/0019* (2013.01); *A61K 47/02* (2013.01); *A61K 47/26* (2013.01); *A61K 47/38* (2013.01); *A61K 9/10* (2013.01); *C07B 2200/13* (2013.01)

(58) Field of Classification Search

None
See application file for complete search history.

(56) References Cited

U.S. PATENT DOCUMENTS

| | | | |
|---|---|---|---|
| 2005/0032836 A1 | 2/2005 | Greco et al. | |
| 2006/0040922 A1 | 2/2006 | Greco et al. | |
| 2006/0229297 A1 | 10/2006 | Csongor et al. | |
| 2011/0178068 A1* | 7/2011 | Almarsson | A61K 31/343 514/428 |

FOREIGN PATENT DOCUMENTS

| | | | | |
|---|---|---|---|---|
| CN | 1136916 C | 2/2004 | | |
| CN | 101801381 A | 8/2010 | | |
| CN | 102596172 A | 7/2012 | | |
| CN | 105218484 A | 1/2016 | | |
| CN | 106543105 A | 3/2017 | | |
| CN | 106699689 A | 5/2017 | | |
| CN | 108261394 A | 7/2018 | | |
| IN | 201721042278 A | 12/2019 | | |
| IN | 201941014547 A | 10/2020 | | |
| WO | 2008139235 A2 | 11/2008 | | |
| WO | 2018229641 A1 | 12/2018 | | |
| WO | 2019016828 A1 | 1/2019 | | |
| WO | WO-2020056929 A1 * | 3/2020 | | C07D 241/04 |

OTHER PUBLICATIONS

Meng English Translation (Year: 2020).*
Huang Eng Translation (Year: 2018).*
The Cleveland Clinic, Psychosis, May 15, 2022 (Year: 2022).*
CN106543105A English Translation (Year: 2017).*
Miyamoto, Seiya et al.; "The Use of Long-Acting Injectable Antipsychotics in Schizophrenia."; Curr Treat Options Psych.; vol. 4; Apr. 19, 2017; pp. 117-126.
Hao, Chao et al., "A New Polymorphic Form of Cariprazine Hydrochloride", Chinese Journal of Pharmaceuticals, vol. 49, No. 6, Dec. 31, 2018, pp. 830-834.
Nagase, Hiroshi, Latest Medicinal Chemistry, vol. 2, Technomic Co., Ltd., Sep. 25, 1999, pp. 347-354, ISBN 4924746800.
Hirayama, Noriaki, Organic Compound Crystallization Handbook—Principles and Know-how-, Maruzen Publishing Co., Ltd., Jul. 25, 2008, pp. 36-43, ISBN 9784621079911.

(Continued)

*Primary Examiner* — Ali Soroush
*Assistant Examiner* — Samantha J Knight
(74) *Attorney, Agent, or Firm* — NKL Law; Allen Xue

(57) ABSTRACT

A pharmaceutical composition containing cariprazine, a preparation method and an application thereof are provided. The pharmaceutical composition contains cariprazine pamoate solid particles. A particle size of the cariprazine solid particles has a Dv(10) less than or equal to 30 microns, a Dv(50) less than or equal to 50 microns, and a Dv(90) less than or equal to 100 microns. When being used, the pharmaceutical composition containing cariprazine is an aqueous suspension and the concentration of the free base of cariprazine is moderate. A long-term effect can be achieved upon injection of a certain administration volume of the pharmaceutical composition, thereby reducing the frequency of medication while increasing patient medication compliance. Furthermore, the pharmaceutical composition has a high bioavailability and has promising marketing prospects.

15 Claims, 23 Drawing Sheets

(56) References Cited

OTHER PUBLICATIONS

Ashizawa, Kazuhide, Optimization of Salt Crystal Form and Crystallization Technology, Pharm Tech Japan, Sep. 1, 2002, vol. 18, No. 10, pp. 81-96.
"Bipolar disorder (manic depressive illness or manic depression)", Harvard Health Publishing. Bipolar Disorder. Mar. 8, 2023, https://www.health.harvard.edu/a_to_z/bipolar-disorder-manic-depressive-illness-or-manic-depression-a-to-z.
Schäfer, Stefan et al., "Failure is an option: learning from unsuccessful proof-of-concept trials", Drug Discovery Today, Nov. 2008, vol. 13, No. 21-22, pp. 913-916.
Hörig, Heidi et al., "From bench to clinic and back: Perspective on the 1st IQPC Translational Research conference", Journal of Translational Medicine, Dec. 20, 2004, vol. 2, No. 1, pp. 1-8.

* cited by examiner

CARIPRAZINE PHARMACEUTICAL COMPOSITION, PREPARATION METHOD AND APPLICATION THEREOF

CROSS-REFERENCE TO RELATED APPLICATIONS

The present application is the U.S. national stage entry of PCT International Application No. PCT/CN2021/114754, filed on Aug. 26, 2021, which claims priority to the following prior applications: the Chinese Patent Application for Invention with the application No. 202010870701.6 filed with China National Intellectual Property Administration on Aug. 26, 2020; the Chinese Patent Application for Invention with the application No. 202010869671.7 filed with China National Intellectual Property Administration on Aug. 26, 2020; the Chinese Patent Application for Invention with the application No. 202110324874.2 filed with China National Intellectual Property Administration on Mar. 26, 2021; and the Chinese Patent Application for Invention with the application No. 202110330670.X filed with China National Intellectual Property Administration on Mar. 26, 2021, the content of each is incorporated herein by reference in its entirety.

TECHNICAL FIELD

The present disclosure relates to the field of chemical medicine, and in particular to a cariprazine-containing pharmaceutical composition, a preparation method therefor and use thereof.

BACKGROUND

Cariprazine hydrochloride, having a chemical structure of the following formula I, is a novel atypical antipsychotic that has antagonistic effect on dopamine D3 receptor, dopamine D2 receptor and 5hydoxytryptamine 2B receptor. It can be used for treating schizophrenia and bipolar I disorder. Cariprazine hydrochloride capsules are currently available on the market. This product is an oral preparation that should be taken daily to maintain its plasma concentration. However, the patient compliance is poor due to required frequent administration.

I

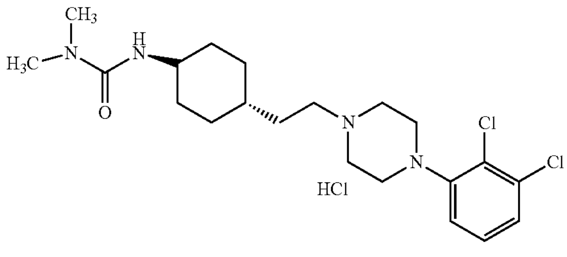

The patent reference CN108261394A discloses an injectable preparation of cariprazine hydrochloride including aqueous suspension form and lyophilizate form, which can achieve a sustained release over at least 1 week or longer. However, the inventors found during research that cariprazine hydrochloride is not very stable in aqueous solution—it will dissociate under slightly acidic to alkaline conditions, and therefore it may dissociate in aqueous suspension, changing the properties and quality of the product and the dissolution and absorption of the drug, and influencing the therapeutic effect of the drug and its medication safety in patients. Moreover, the administration concentration of cariprazine in the injectable preparation of cariprazine hydrochloride and the plasma concentration in the pK experiments on animals disclosed in the patent reference CN108261394A are too high. Given that cariprazine clearance considerably varies in species as shown by original research data (about 2-4 hours in rats, and 3-9 days in humans), an excessive plasma concentration may cause stronger toxic and side effects and excessive drug accumulation in the human body.

No injectable preparations of very slightly soluble salts of cariprazine with improved properties have now been reported.

SUMMARY

To ease the problems in the prior art, the present disclosure provides a pharmaceutical composition of cariprazine, which comprises solid particles of cariprazine that have particle sizes Dv(10) of ≤30 microns, Dv(50) of ≤50 microns and Dv(90) of ≤100 microns, preferably ≤10 microns.

According to an embodiment of the present disclosure, the solid particles of cariprazine may be selected from solid particles of cariprazine, a pharmaceutically acceptable salt of cariprazine and a solvate thereof.

According to an embodiment of the present disclosure, the solvate may be selected from a hydrate.

According to an embodiment of the present disclosure, the pharmaceutically acceptable salt of cariprazine comprises, but is not limited to, cariprazine embonate.

According to an embodiment of the present disclosure, the embonic acid is also known as pamoic acid, CAS No. 130-85-8.

According to an embodiment of the present disclosure, the solid particles of cariprazine may be in crystalline or amorphous form.

According to an embodiment of the present disclosure, the cariprazine embonate is crystalline form A of cariprazine embonate.

According to an embodiment of the present disclosure, an X-ray powder diffraction graph of the crystalline form A of cariprazine embonate has characteristic peaks at 2θ values of 13.1°±0.2°, 18.7°±0.2°, 21.0°±0.2°, etc.

Further, an X-ray powder diffraction graph of the crystalline form A of cariprazine embonate has characteristic peaks at 2θ values of 4.8°±0.2°, 13.1°±0.2°, 18.7°±0.2°, 20.1°±0.2°, 21.0°±0.2°, 26.1°±0.2°, etc.

Further, an X-ray powder diffraction graph of the crystalline form A of cariprazine embonate has characteristic peaks at 2θ values of 4.8°±0.2°, 9.7±0.2°, 12.3°±0.2°, 13.1°±0.2°, 18.7°±0.2°, 20.1°±0.2°, 21.0°±0.2°, 26.1°±0.2°, etc.

Furthermore, an X-ray powder diffraction graph of the crystalline form A of cariprazine embonate has absorption peaks at 2θ values of 4.8°±0.2°, 8.2°±0.2°, 9.7±0.2°, 11.6°±0.2°, 12.3°±0.2°, 13.1°±0.2°, 14.7°±0.2°, 15.1°±0.2°, 16.6°±0.2°, 18.7°±0.2°, 20.1°±0.2°, 20.7°±0.2°, 21.0°±0.2°, 21.6°±0.2°, 22.1°±0.2°, 24.1°±0.2°, 26.1°±0.2°, etc.

Furthermore, an X-ray powder diffraction graph of the crystalline form A of the cariprazine embonate is substantially as shown in FIG. 2.

A differential scanning calorimetry analysis graph of the crystalline form A of cariprazine embonate is substantially as shown in FIG. 3, indicating a melting point of about 166.5° C.

A thermogravimetric analysis graph of the crystalline form A of cariprazine embonate is substantially as shown in FIG. 4, indicating two weight losses before 115° C., which are attributed to the loss of surface solvent and channel water, and a weight loss of about 1.1% at 115-165° C., which is attributed to the loss of water of crystallization.

A nuclear magnetic resonance graph of the crystalline form A of cariprazine embonate is substantially as shown in FIG. 5, indicating that cariprazine and embonic acid form the salt in a molar ratio of 1:1.

According to an embodiment of the present disclosure, a preparation method for the crystalline form A of cariprazine embonate is as follows:

(1) adding cariprazine embonate to a solvent, and stirring the mixture so cariprazine embonate crystallizes to form the crystalline form A of cariprazine embonate;

wherein the solvent is methanol;

(2) dissolving cariprazine embonate in a good solvent, adding gradually an antisolvent, and stirring the mixture so cariprazine embonate crystallizes to form the crystalline form A of cariprazine embonate;

wherein the good solvent is dibutyl ketone;

the antisolvent is n-heptane.

According to an embodiment of the present disclosure, the cariprazine embonate is crystalline form F of cariprazine embonate.

According to an embodiment of the present disclosure, an X-ray powder diffraction graph of the crystalline form F of cariprazine embonate has characteristic peaks at 2θ values of 4.9°±0.2°, 19.2°±0.2°, 21.0°±0.2°, etc.

Further, an X-ray powder diffraction graph of the crystalline form F of cariprazine embonate has characteristic peaks at 2θ values of 4.9°±0.2°, 13.6°±0.2°, 19.2°±0.2°, 21.0°±0.2°, 24.0°±0.2°, 26.3°±0.2°, etc.

Further, an X-ray powder diffraction graph of the crystalline form F of cariprazine embonate has characteristic peaks at 2θ values of 4.9°±0.2°, 12.8°±0.2°, 13.6°±0.2°, 19.2°±0.2°, 20.3°±0.2°, 21.0°±0.2°, 24.0°±0.2°, 26.3°±0.2°, etc.

Furthermore, according to an embodiment of the present disclosure, an X-ray powder diffraction graph of the crystalline form F of cariprazine embonate has characteristic peaks at 2θ values of 4.9°±0.2°, 8.4°±0.2°, 9.7±0.2°, 10.4°±0.2°, 11.6°±0.2°, 12.8°±0.2°, 13.3°±0.2°, 13.6°±0.2°, 15.4°±0.2°, 16.8°±0.2°, 17.0°±0.2°, 18.5°±0.2°, 18.8°±0.2°, 19.2°±0.2°, 19.5°±0.2°, 21.0°±0.2°, 21.9°±0.2°, 22.2°±0.2°, 22.5°±0.2°, 24.0°±0.2°, 25.1°±0.2°, 25.7°±0.2°, 26.3°±0.2°, 26.8°±0.2°, 28.8°±0.2°, 29.6°±0.2°, etc.

Furthermore, an X-ray powder diffraction graph of the crystalline form F of the cariprazine embonate is substantially as shown in FIG. 6.

A differential scanning calorimetry analysis graph of the crystalline form F of cariprazine embonate is substantially as shown in FIG. 7, indicating a melting point of about 166.6° C.

A thermogravimetric analysis graph of the crystalline form F of cariprazine embonate is substantially as shown in FIG. 8, indicating a weight loss of about 1.3% before 115° C., which is attributed to the loss of channel water, and a weight loss of about 1.3% at 115-175° C., which is attributed to the loss of water of crystallization.

A nuclear magnetic resonance graph of the crystalline form F of cariprazine embonate is substantially as shown in FIG. 9, indicating that cariprazine and embonic acid form the salt in a molar ratio of 1:1.

According to an embodiment of the present disclosure, a preparation method for the crystalline form F of cariprazine embonate is as follows:

forming a slurry of crystalline form A of cariprazine embonate in a solvent, stirring the slurry so cariprazine embonate crystallizes to form the crystalline form F of cariprazine embonate;

wherein the solvent is ethyl acetate, isopropyl acetate, methyl tert-butyl ether or n-heptane.

According to an embodiment of the present disclosure, the cariprazine embonate is crystalline form D of cariprazine embonate.

According to an embodiment of the present disclosure, an X-ray powder diffraction graph of the crystalline form D of cariprazine embonate has characteristic peaks at 2θ values of 9.6°±0.2°, 11.9°±0.2°, 20.4°±0.2°, etc.

Further, an X-ray powder diffraction graph of the crystalline form D of cariprazine embonate has characteristic peaks at 2θ values of 9.6°±0.2°, 11.9°±0.2°, 16.6°±0.2°, 20.4°±0.2°, 24.5°±0.2°, 25.3°±0.2°, etc.

Further, an X-ray powder diffraction graph of the crystalline form D of cariprazine embonate has characteristic peaks at 2θ values of 9.6°±0.2°, 11.9°±0.2°, 15.2°±0.2°, 16.6°±0.2°, 20.4°±0.2°, 20.7°±0.2°, 24.5°±0.2°, 25.3°±0.2°, etc.

Furthermore, according to an embodiment of the present disclosure, an X-ray powder diffraction graph of the crystalline form D of cariprazine embonate has characteristic peaks at 2θ values of 9.6°±0.2°, 10.1°±0.2°, 10.5±0.2°, 11.9°±0.2°, 13.2°±0.2°, 14.5°±0.2°, 15.2°±0.2°, 16.6°±0.2°, 20.4°±0.2°, 20.7°±0.2°, 21.1°±0.2°, 21.9°±0.2°, 23.5°±0.2°, 24.5°±0.2°, 25.3°±0.2°, etc.

Furthermore, an X-ray powder diffraction graph of the crystalline form D of the cariprazine embonate is substantially as shown in FIG. 10.

A differential scanning calorimetry analysis graph of the crystalline form D of cariprazine embonate is substantially as shown in FIG. 11, indicating a melting point of about 164.6° C.

A thermogravimetric analysis graph of the crystalline form D of cariprazine embonate is substantially as shown in FIG. 12, indicating a weight loss of about 4% before 190° C., which is attributed to the loss of water and ethanol.

A nuclear magnetic resonance graph of the crystalline form D of cariprazine embonate is substantially as shown in FIG. 13, indicating that cariprazine and embonic acid form the salt in a molar ratio of 1:1.

According to an embodiment of the present disclosure, a preparation method for the crystalline form D of cariprazine embonate is as follows:

stirring cariprazine embonate in ethanol so cariprazine embonate crystallizes to form the crystalline form D of cariprazine embonate.

According to an embodiment of the present disclosure, the cariprazine embonate is crystalline form B of cariprazine embonate.

According to an embodiment of the present disclosure, an X-ray powder diffraction pattern of the crystalline form B of cariprazine embonate has characteristic peaks at 2θ values of 5.2°±0.2°, 10.5°±0.2°, 14.0°±0.2°, 14.4°±0.2°, 17.5°±0.2°, 21.3°±0.2°, 21.9°±0.2°, 22.9°±0.2°, 26.2°±0.2°, etc.

Further, an X-ray powder diffraction graph of the crystalline form B of the cariprazine embonate is substantially as shown in FIG. 14.

According to an embodiment of the present disclosure, the cariprazine embonate is crystalline form C of cariprazine embonate.

According to an embodiment of the present disclosure, an X-ray powder diffraction pattern of the crystalline form C of cariprazine embonate has characteristic peaks at 2θ values of 8.6°±0.2°, 13.0°±0.2°, 16.8°±0.2°, 17.3°±0.2°, 18.2°±0.2°, 18.5°±0.2°, 19.8°±0.2°, 22.1°±0.2°, 23.5°±0.2°, etc. Further, an X-ray powder diffraction graph of the crystalline form C of the cariprazine embonate is substantially as shown in FIG. 15.

According to an embodiment of the present disclosure, the cariprazine embonate is crystalline form E of cariprazine embonate.

According to an embodiment of the present disclosure, an X-ray powder diffraction pattern of the crystalline form E of cariprazine embonate has characteristic peaks at 2θ values of 11.0°±0.2°, 12.8°±0.2°, 13.8°±0.2°, 15.5°±0.2°, 15.9°±0.2°, 17.9°±0.2°, 18.4°±0.2°, 20.7°±0.2°, 23.4°±0.2°, etc. Further, an X-ray powder diffraction graph of the crystalline form E of the cariprazine embonate is substantially as shown in FIG. 16.

According to an embodiment of the present disclosure, the cariprazine embonate is crystalline form G of cariprazine embonate.

According to an embodiment of the present disclosure, an X-ray powder diffraction pattern of the crystalline form G of cariprazine embonate has characteristic peaks at 2θ values of 8.7°±0.2°, 10.0°±0.2°, 13.6°±0.2°, 14.3°±0.2°, 17.5°±0.2°, 18.0°±0.2°, 20.3°±0.2°, 23.2°±0.2°, 25.1°±0.2°, etc.

Further, an X-ray powder diffraction graph of the crystalline form G of the cariprazine embonate is substantially as shown in FIG. 17.

According to an embodiment of the present disclosure, the cariprazine embonate is crystalline form I of cariprazine embonate.

According to an embodiment of the present disclosure, an X-ray powder diffraction pattern of the crystalline form I of cariprazine embonate has characteristic peaks at 2θ values of 10.0°±0.2°, 14.9°±0.2°, 16.3°±0.2°, 17.7°±0.2°, 18.5°±0.2°, 19.0°±0.2°, 21.1°±0.2°, 22.1°±0.2°, 24.5°±0.2°, etc. Further, an X-ray powder diffraction graph of the crystalline form I of the cariprazine embonate is substantially as shown in FIG. 18.

According to an embodiment of the present disclosure, the pharmaceutical composition of cariprazine may further comprise an auxiliary material, which may be selected from one or more of a suspending agent, a wetting agent, an osmotic pressure regulator, a solvent, a stabilizer, a buffer and a surfactant.

According to an embodiment of the present disclosure, the suspending agent is at a concentration in the range of 0 mg/mL to 10 mg/mL, preferably 3.5 mg/mL to 5 mg/mL, for example, 3.5 mg/mL, 4.0 mg/mL, 4.5 mg/mL or 5.0 mg/mL.

According to an embodiment of the present disclosure, the suspending agent is selected from one or more of sodium carboxymethylcellulose, methylcellulose and polyvinylpyrrolidone, preferably sodium carboxymethylcellulose.

According to an embodiment of the present disclosure, the wetting agent is at a concentration in the range of 1 mg/mL to 10 mg/mL, preferably 1 mg/mL to 5 mg/mL, for example, 1 mg/mL, 1.5 mg/mL, 2.0 mg/mL, 2.5 mg/mL, 3.0 mg/mL, 3.5 mg/mL, 4.0 mg/mL, 4.5 mg/mL or 5.0 mg/mL.

According to an embodiment of the present disclosure, the wetting agent is selected from one or more of tween 20, tween 80 and poloxamer 188, preferably tween 20.

According to an embodiment of the present disclosure, the osmotic pressure regulator is at a concentration in the range of 20 mg/mL to 30 mg/mL, preferably 23 mg/mL to 26 mg/mL, for example, 23 mg/mL, 24.7 mg/mL or 26 mg/mL.

According to an embodiment of the present disclosure, the osmotic pressure regulator is selected from one or more of sodium chloride, mannitol and sucrose.

According to an embodiment of the present disclosure, the stabilizer is at a concentration in the range of 0 mg/mL to 30 mg/mL, preferably 1 mg/mL to 10 mg/mL, for example, 1 mg/mL, 3 mg/mL, 5 mg/mL or 7.0 mg/mL.

According to an embodiment of the present disclosure, the stabilizer is PVP K12.

According to an embodiment of the present disclosure, the buffer is selected from one or more of phosphoric acid, phosphate, citric acid, sodium citrate, hydrochloric acid and sodium hydroxide.

According to an embodiment of the present disclosure, the surfactant is sodium deoxycholate.

According to an embodiment of the present disclosure, the solvent is water, for example, water for injection.

By way of example, the cariprazine composition may comprise:

(a) cariprazine embonate;
(b) sodium carboxymethylcellulose;
(c) tween 20;
(d) disodium phosphate;
(e) monosodium phosphate; and
(f) mannitol;

and, optionally, the cariprazine composition may comprise sodium hydroxide or hydrochloric acid.

According to an embodiment of the present disclosure, the cariprazine composition is a cariprazine injection, such as a long-acting cariprazine injection.

According to an embodiment of the present disclosure, in the cariprazine composition or long-acting cariprazine injection, the solid particles of cariprazine are at a concentration of no less than 15 mg/mL.

According to an embodiment of the present disclosure, a preparation method for the cariprazine composition comprises the following steps:

(1) dissolving the wetting agent, buffering agent and osmotic pressure regulator in a solvent;
(2) adding the solid particles of cariprazine to obtain an aqueous suspension of coarse particles;
(3) grinding the aqueous suspension of coarse particles described above with a ball mill to obtain a suspension; and
(4) adding the suspending agent to the suspension described above, mixing the suspension homogeneously, adjusting the pH to 4.0-9.0 with sodium hydroxide or hydrochloric acid, and bringing the suspension to volume to obtain an aqueous suspension.

According to an embodiment of the preparation method of the present disclosure, in step (1), the wetting agent, buffer and osmotic pressure regulator may be sequentially dissolved in the solvent, for example, in water for injection.

According to an embodiment of the preparation method of the present disclosure, in step (4), the pH may be adjusted to 4.0, 4.5, 5.0, 5.5, 6.0, 6.5, 7.0, 7.5, 8.0, 8.5 or 9.0.

The present disclosure provides use of the pharmaceutical composition of cariprazine for manufacturing a medicament for treating and/or preventing psychosis, bipolar disorder and acute mania.

The present disclosure also provides a method for treating and/or preventing psychosis, bipolar disorder and acute mania, which comprises administering the pharmaceutical composition of cariprazine to a patient in need.

According to an embodiment of the present disclosure, the "Dv(10)", "Dv(50)" and "Dv(90)" refer to volume-weighted particle diameters, wherein cumulative 10 v/v %, 50 v/v % or 90 v/v % of the particles have equal or smaller diameters when measured. For example, if the Dv(50) of a population of particles is about 25 microns, then 50% by volume of the particles have a diameter of less than or equal to about 25 microns.

The preferred conditions described above may be combined by those skilled in the art to obtain preferred embodiments of the present disclosure without departing from the spirit of the present disclosure.

The reagents and starting materials used in the present disclosure are commercially available.

According to an embodiment of the present disclosure, the room temperature refers to an ambient temperature of 10-35° C.

Advantageous Effects

After extensive research, screening and trials, the inventors finally find that cariprazine embonate, one of the very slightly soluble salts of cariprazine, has the advantages of long-acting sustained-release preparations and can develop into a suspension for injection while the risk of dissociation with cariprazine hydrochloride can be overcome and a long-acting effect, as well as relatively low plasma concentrations in rats, can be achieved, greatly improving patient compliance and the bioavailability and medication safety of drugs.

The characteristics of the pharmaceutical composition of cariprazine of the present disclosure comprise sustained release, high bioavailability, good stability in solution, small-volume administration, etc. After one dose, the release of cariprazine can last at least a week or longer. The pharmaceutical composition of cariprazine of the present disclosure has a good marketing prospect.

DETAILED DESCRIPTION

Figure 1:
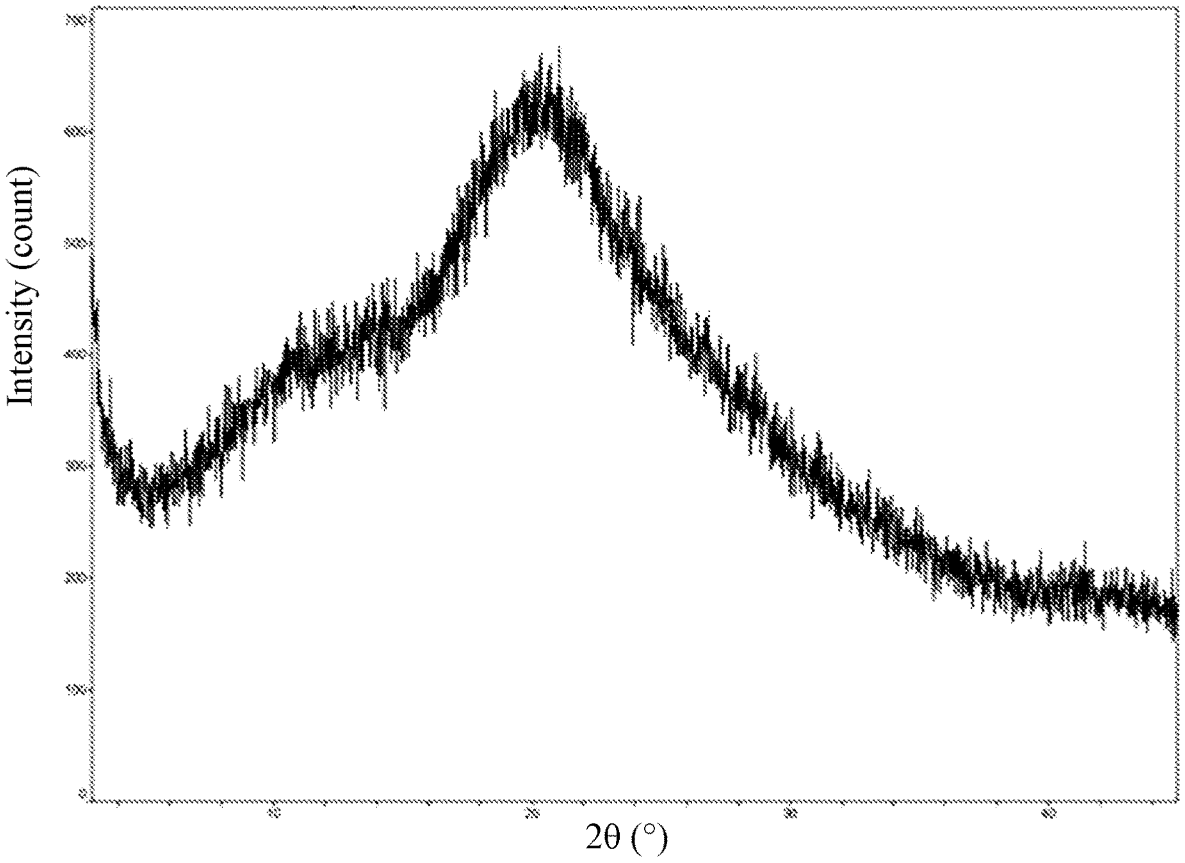
FIG. 1 is an XRPD graph of amorphous cariprazine embonate.

The present disclosure is further illustrated by the following examples; however, these examples should not be construed as limiting the present disclosure. Experimental procedures without specified conditions in the following examples are conducted in accordance with conventional procedures and conditions, or in accordance with the manufacturer's manual.

Unless otherwise indicated, the starting materials and reagents in the examples below are either commercially available or prepared by one skilled in the art according to methods known in the art.

The salt compounds of the examples were tested by nuclear magnetic resonance ($^1$H-NMR), X-ray powder diffraction (XRPD), differential scanning calorimetry (DSC), thermogravimetric analysis (TGA), hot-stage polarized light microscopy (PLM) and high performance liquid chromatography (HPLC), and the test parameters are as follows:

(1) The $^1$H-NMR measurements were taken on a Bruker Advance III500M nuclear magnetic resonance spectrometer at a frequency of 400 Mz with deuterated DMSO as the solvent.

(2) The DSC measurements were taken on a sealed pan device in TA Instruments model Q2000: samples (about 1-2 mg) were weighed in aluminum pans and transferred to the instrument for measurement. The test parameters are as follows: the instrument was equilibrated at 30° C. and heated to 300° C. at a rate of 10° C./min, data was collected, and the experiments were conducted in a nitrogen atmosphere.

(3) The TGA measurements were taken on a TA Instruments model Q500 device: samples (about 2-5 mg) were weighed in aluminum pans and transferred to the instrument for measurement. The test parameters are as follows: the instrument was heated to 350° C. at a rate of 10° C./min, data was collected, and the experiments were conducted in a nitrogen atmosphere.

(4) The XRPD measurements were taken on a Bruker model D8 Advance X-ray powder diffractometer using a round zero background single crystal silicon sample stage. The scan parameters are as follows: voltage, 40 kv; current, 40 mA; scan range, 3-45°; scan increment, 0.02°; scan mode, continuous scan.

(5) The PLM analyses were performed under a model DYP990/TPH350 hot stage polarizing microscope from Shanghai Dian Ying Optical Instruments: a small amount of sample was dispersed in a glass slide and photographed using an eyepiece lens at a magnification of 10× and an objective lens at a magnification of 5-40×.

(6) Methods of measuring HPLC content and detecting related substances:

Content Method

| | |
|---|---|
| Instrument | High performance liquid chromatography |
| Chromatography column | Welch Ultimate ® XB-C18 4.6 × 250 mm, 5 μm |
| Detection wavelength | 217 nm |
| Flow rate | 1.0 mL/min |
| Column temperature | 30° C. |
| Injection volume | 5 μL |
| Mobile phase A | 0.025 mol/L monopotassium phosphate solution (pH = 2.4) |
| Mobile phase B | Acetonitrile |
| Solvent | 80% methanol |

Content Gradient Elution Program Table

| Time (min) | Mobile phase A (%) | Mobile phase B (%) |
|---|---|---|
| 0 | 60 | 40 |
| 2 | 40 | 60 |
| 5 | 15 | 85 |
| 5.1 | 60 | 40 |
| 10 | 60 | 40 |

Related Substances Method

| | |
|---|---|
| Instrument | High performance liquid chromatography |
| Chromatography column | Welch Ultimate ® XB-C18 4.6 × 250 mm, 5 μm |
| Detection wavelength | 217 nm |
| Flow rate | 1.0 ml/min |
| Column temperature | 30° C. |
| Injection volume | 10 μl |

-continued

| | |
|---|---|
| Mobile phase A | 0.025 mol/L monopotassium phosphate solution (pH = 2.4) |
| Mobile phase B | Acetonitrile |
| Solvent | 80% methanol |

Related Gradient Elution Program Table

| Time (min) | Mobile phase A (%) | Mobile phase B (%) |
|---|---|---|
| 0 | 80 | 20 |
| 7 | 45 | 55 |
| 17 | 37 | 63 |
| 25 | 20 | 80 |
| 25.1 | 80 | 20 |
| 35 | 80 | 20 |

Unless otherwise indicated, the aqueous suspensions of the pharmaceutical composition of cariprazine in the context of the present disclosure were measured on a particle size analyzer under the following conditions:

| | |
|---|---|
| Injector: SCF-105B | Substance: cariprazine composition |
| Refractive index of particles: 1.595 | Refractive index of dispersant: 1.333 |
| Dispersant: water | Background test time: 10 s |
| Sample test time: 10 s | Obscuration: 10-20% |
| Stirring speed: 700-2000 r/min | Analysis model: universal |
| Measurement range: 0.02-2100 μm | Particle absorption rate: 0.1 |

Measurement was performed in triplicate, and a mean value was produced.

Example 1: Preparation of Cariprazine Embonate 4000 mg (9.36 mmol) of cariprazine was dissolved in 200 mL of a phosphoric acid solution (5.4 mg/mL) to give solution A. 3634 mg (9.36 mmol) of embonic acid was dissolved in 100 mL of a sodium hydroxide solution (7.5 mg/mL) to give solution B. 100 mL of solution B was added to 200 mL of solution A over 30 min under stirring. The product was isolated by filtration, washed with water and dried in vacuo at 40° C. for 12 h to give a pale yellow solid (5840 mg, 76% yield (calculated based on free base)).

The structure and molar ratio of the cariprazine embonate of the present disclosure were confirmed by hydrogen nuclear magnetic resonance.

$^1$H-NMR (400 MHz, DMSO-d6): δ8.38 (s, 2H), 8.16 (d, 2H), 8.80 (d, 2H), 7.39-7.13 (m, 7H), 5.86 (d, 1H), 4.76 (s, 2H), 3.40-3.32 (m, 3H), 3.22-3.18 (m, 4H), 2.75 (s, 6H), 1.76 (t, 4H), 1.63-1.57 (m, 2H), 1.25-1.16 (m, 3H), 1.04-0.96 (m, 2H).

The nuclear magnetic resonance result shows that cariprazine and embonic acid formed the salt in a molar ratio of 1:1.

The sample described above was analyzed by solid-state characterization. The XRPD graph is shown in FIG. 1. The result indicates an amorphous form.

Example 2: Preparation of Amorphous Cariprazine Embonate 20 g (46.8 mmol) of cariprazine and 18.17 g (46.8 mmol) of embonic acid were dissolved in 170 mL of a mixed solvent of THF:MeOH (2:1) at 60° C. The mixture was filtered and concentrated under reduced pressure to remove the solvent, and then 300 mL of methanol was added to dissolve the residue at 60° C. The solution was concentrated under reduced pressure to remove the solvent, and the residue was dried in vacuo at 40° C. for 12 h to give amorphous cariprazine embonate (36.6 g).

Example 3: Preparation of Cariprazine Hemiembonate 200 mg (0.468 mmol) of cariprazine was dissolved in 10 mL of a phosphoric acid solution (5.4 mg/mL) to give solution A. 90.85 mg (0.234 mmol) of embonic acid was dissolved in 2.5 mL of a sodium hydroxide solution (7.5 mg/mL) to give solution B. 2.5 mL of solution B was added to 10 mL of solution A over 30 min under stirring. The product was isolated by filtration, washed with water and dried in vacuo at 40° C. for 12 h to give a pale yellow solid (204 mg, 70% yield). The structure and molar ratio of the cariprazine embonate of the present disclosure were confirmed by hydrogen nuclear magnetic resonance.

$^1$H-NMR (400 MHz, DMSO-d6): δ8.25 (s, 1H), 8.18 (d, 1H), 7.69 (d, 1H), 7.38-7.31 (m, 2H), 7.22-7.14 (m, 2H), 7.05 (t, 1H), 5.86 (d, 1H), 4.71 (s, 1H), 3.39-3.22 (m, 5H), 2.75 (s, 6H), 1.75 (t, 4H), 1.59-1.54 (m, 2H), 1.25-1.15 (m, 3H), 1.04-0.95 (m, 2H).

The nuclear magnetic resonance result shows that cariprazine and embonic acid formed the salt in a molar ratio of 2:1.

The sample described above was analyzed by PLM, and the result shows that the sample was an amorphous solid without light polarization.

Example 4: Preparation of Cariprazine 1-Hydroxy-2-Naphthoate 100 mg (0.234 mmol) of cariprazine and 45 mg (0.234 mmol) of 1-hydroxy-2-naphthoic acid were added to 8 mL of methanol, completely dissolved by stirring and filtered. Three volumes of n-heptane were added. The solvent was evaporated at room temperature to give an oil. The oil was dried in vacuo at 40° C. for 4 h to give a solid.

PLM analysis showed that the solid had light polarization and started to melt at about 200° C. $^1$H-NMR (400 MHz, DMSO-d6): δ8.23 (d, 1H), 7.80-7.74 (m, 2H), 7.57-7.53 (m, 1H), 7.48-7.44 (m, 1H), 7.38-7.31 (m, 2H), 7.20-7.16 (m, 2H), 5.86 (d, 1H), 3.36-3.09 (m, 10H), 2.75 (s, 6H), 1.74 (t, 4H), 1.61-1.56 (m, 2H), 1.33-1.15 (m, 5H), 1.02-0.83 (m, 3H).

The nuclear magnetic resonance result shows that cariprazine and 1-hydroxy-2-naphthoic acid formed the salt in a molar ratio of 1:1.

Example 5: Preparation of Cariprazine Laurate 50 mg (0.117 mmol) of cariprazine and 23.7 mg (0.118 mmol) of lauric acid were added to 5 mL of methanol and dissolved at 50° C. The solution was stirred at room temperature for 12 h. Two volumes of water were added. The mixture was filtered. The solid was dried in vacuo at 40° C. for 12 h to give cariprazine laurate.

Example 6: Preparation of Cariprazine Palmitate 50 mg (0.117 mmol) of cariprazine and 30.3 mg (0.118 mmol) of palmitic acid were added to 5 mL of methanol and dissolved at 50° C. The solution was stirred at room temperature for 12 h. One volume of water was added. The mixture was filtered. The solid was dried in vacuo at 40° C. for 12 h to give cariprazine palmitate.

Example 7: Preparation of Cariprazine Sebacate, Cariprazine Succinate, Cariprazine Malate, Cariprazine Lactate, Cariprazine Undecanoate and Cariprazine Heptanoate Cariprazine and acid were measured out in a molar ratio of 1:1.1. Each acid was dissolved in methanol solvent, and the resulting acidic reagent was added to a solution of cariprazine in methanol at room temperature to start a salt formation reaction. After 12 h of stirring at room temperature, the solvent was left to volatilize at room temperature, and the residue was dried to give the corresponding salt of cariprazine.

Example 8: Preparation of Crystalline Form A of Cariprazine Embonate 2000 mg of the cariprazine embonate prepared in Example 1 was measured out and added to 20 mL of methanol. The mixture was stirred at room temperature for 24 h to crystallize cariprazine embonate. The solid was collected by filtration and dried in vacuo at 55° C. to give crystalline form A of cariprazine embonate (1900 mg, 95% yield).

Figure 2:
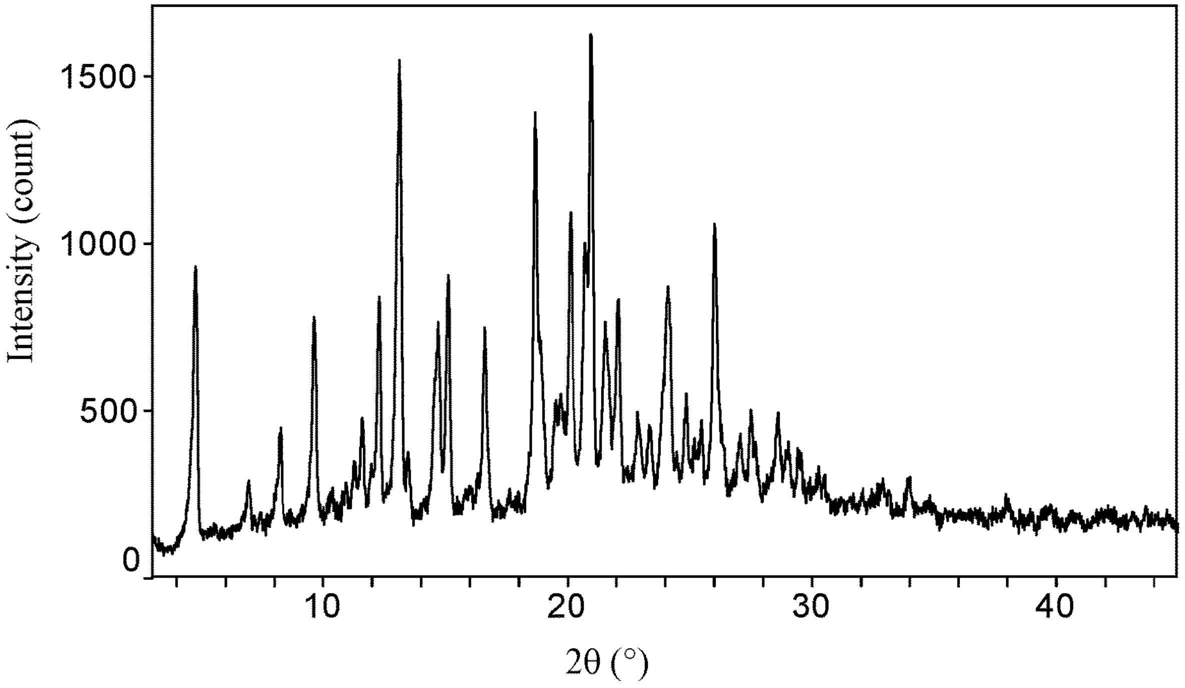
FIG. 2 is an XRPD graph of crystalline form A of cariprazine embonate.

Its X-ray powder diffraction graph is shown in FIG. 2.

Figure 3:
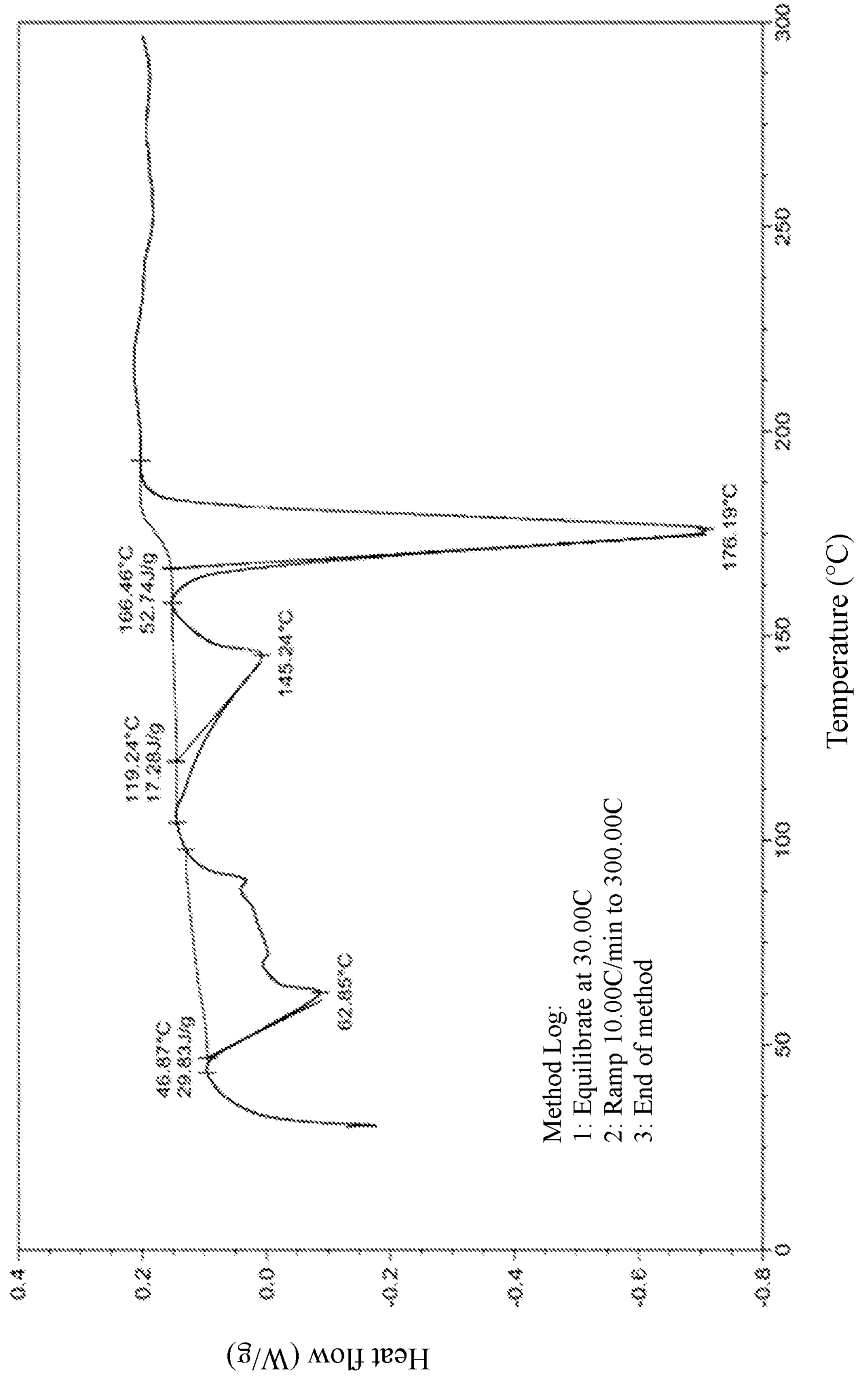
FIG. 3 is a DSC graph of crystalline form A of cariprazine embonate.
Figure 4:
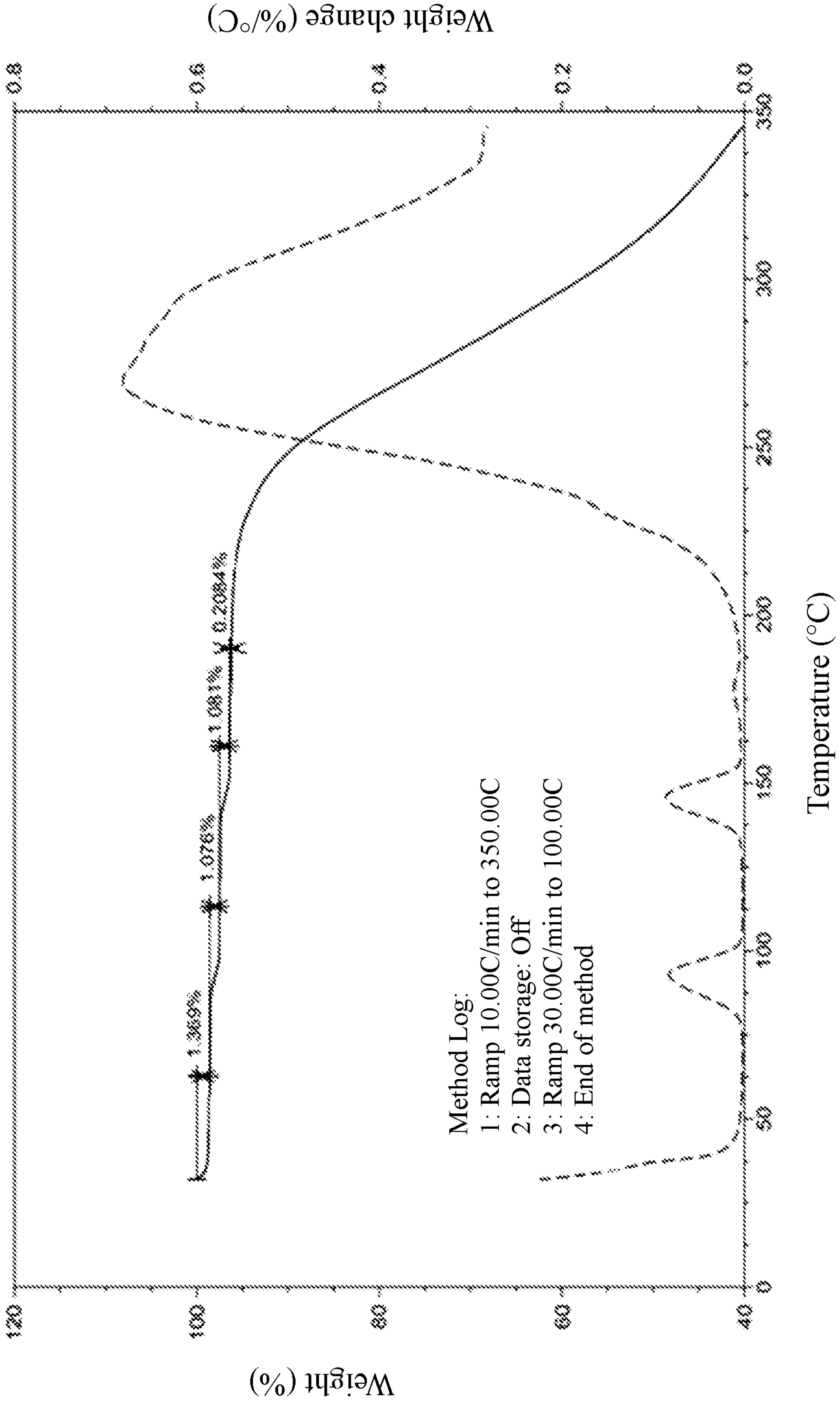
FIG. 4 is a TGA graph of crystalline form A of cariprazine embonate.

Its differential scanning calorimetry graph is shown in FIG. 3, indicating a melting point of 166.5° C. Its thermogravimetric analysis graph is shown in FIG. 4, indicating two weight losses before 115° C., which are attributed to the loss of surface solvent and channel water, and a weight loss of about 1.1% at 115-165° C., which is attributed to the loss of water of crystallization.

Figure 5:
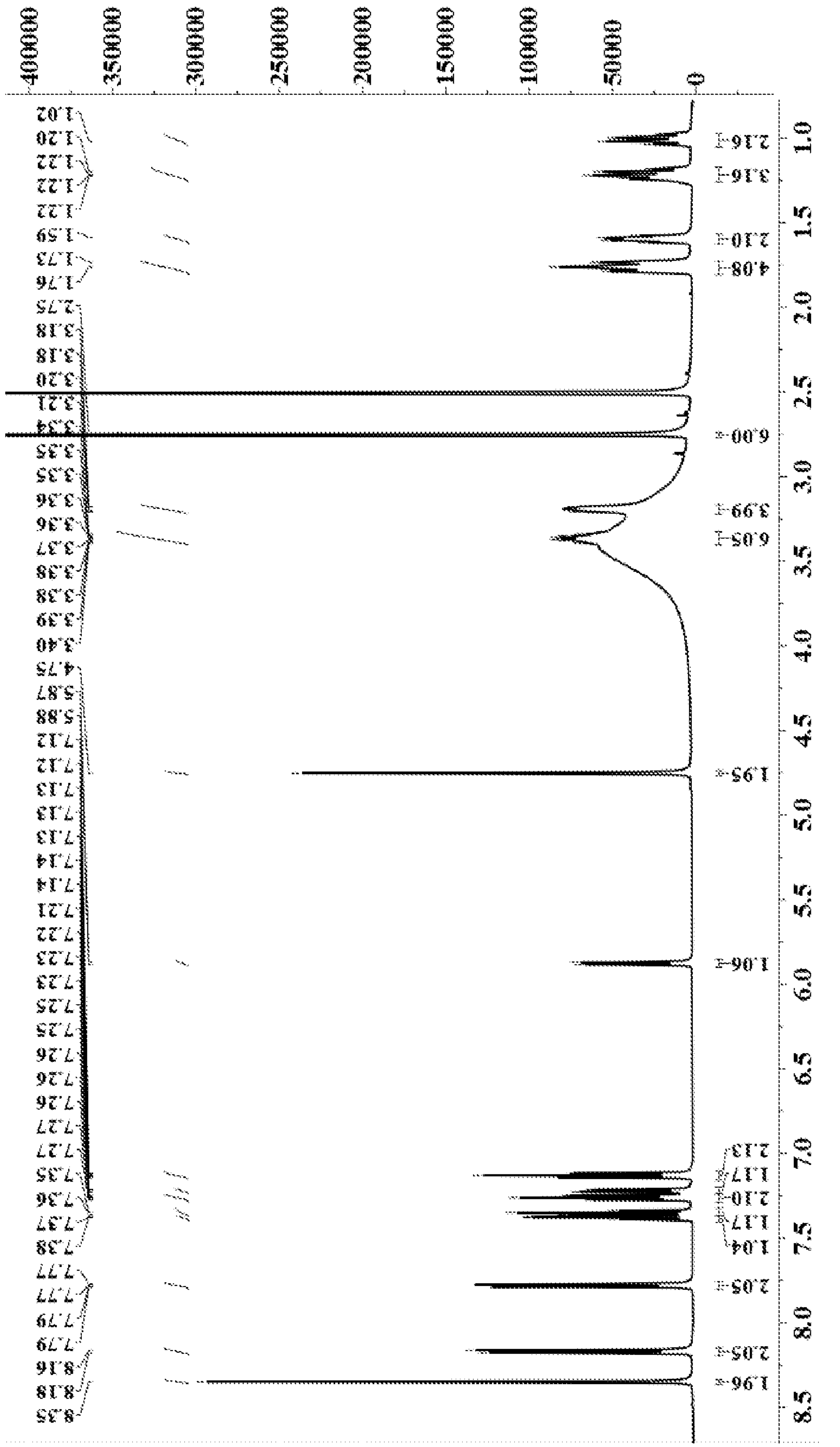
FIG. 5 is a $^1$H-NMR graph of crystalline form A of cariprazine embonate.

Its nuclear magnetic resonance graph is shown in FIG. 5, indicating that cariprazine and embonic acid formed the salt in a molar ratio of 1:1.

Example 9: Preparation of Crystalline Form A of Cariprazine Embonate

A 30 g sample of the amorphous solid of cariprazine embonate prepared in Example 2 was measured out and added to 300 mL of methanol. The mixture was stirred at 10° C. for 24 h to crystallize cariprazine embonate. The solid was collected by filtration and dried in vacuo at 55° C. to give crystalline form A of cariprazine embonate (28.5 g).

Example 10: Preparation of Crystalline Form B of Cariprazine Embonate 200 mg of the crystalline form A of cariprazine embonate obtained in Example 9 was measured out and a slurry of it was formed in methanol solvent. In the slurry, the weight-to-volume ratio of crystalline form A of cariprazine embonate to solvent was 40 mg/mL. The slurry was stirred for 3 days so cariprazine embonate crystallized to form crystalline form B of cariprazine embonate (180 mg).

Figure 14:
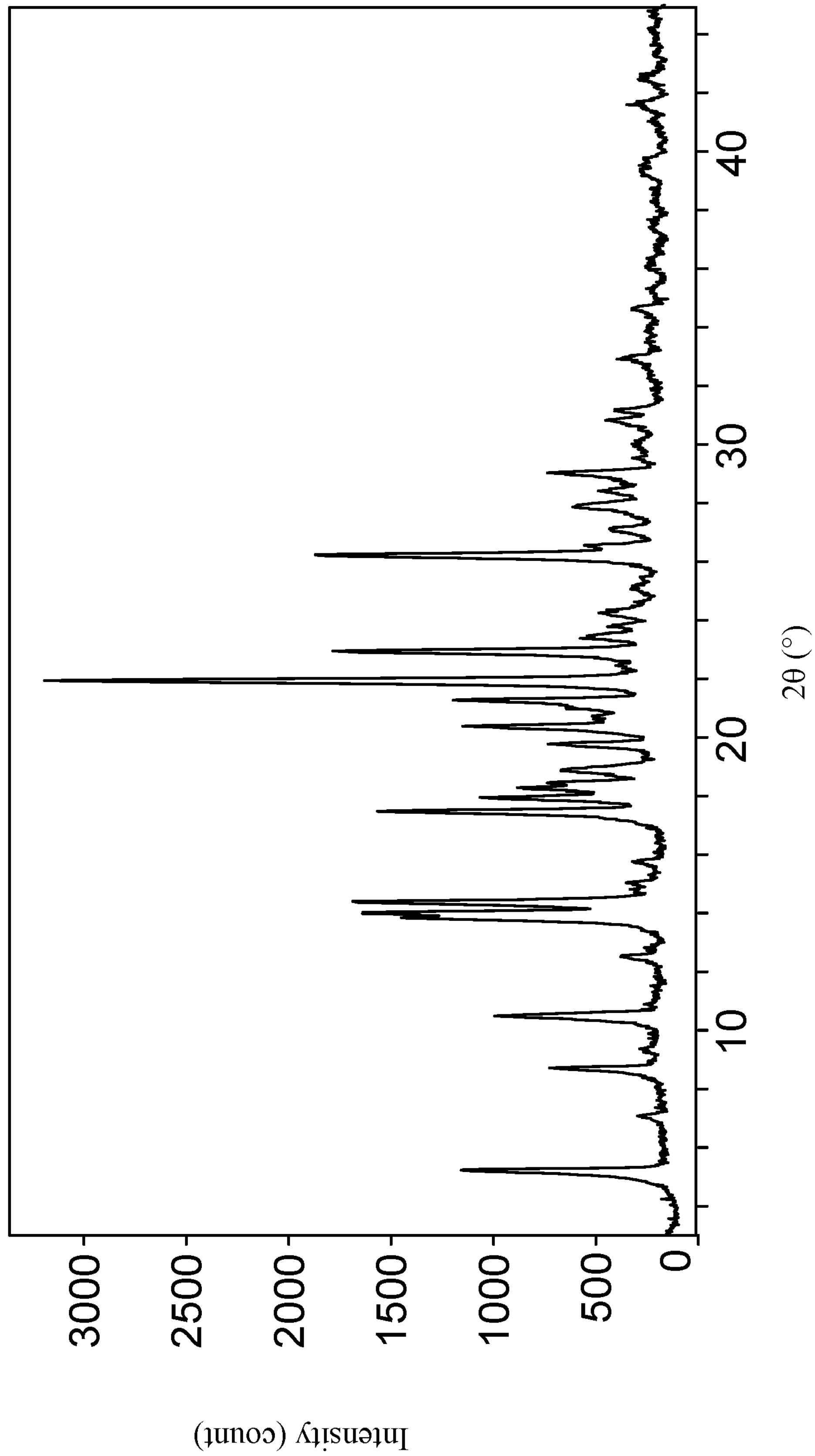
FIG. 14 is an XRPD graph of crystalline form B of cariprazine embonate.

Its X-ray powder diffraction graph is shown in FIG. 14.

Its nuclear magnetic resonance result shows that it was a methanol solvate.

Example 11: Preparation of Crystalline Form B of Cariprazine Embonate 2 g of the crystalline form A of cariprazine embonate prepared in Example 9 was measured out and added to 50 mL of methanol. The mixture was stirred at room temperature for 72 h to crystallize cariprazine embonate. The solid was collected by filtration and dried in vacuo at 55° C. to give crystalline form B of cariprazine embonate (1.9 mg).

Example 12: Preparation of Crystalline Form C of Cariprazine Embonate

The crystalline form A of cariprazine embonate obtained in Example 8 was measured out and a slurry of it was formed in acetone solvent. In the slurry, the weight-to-volume ratio of crystalline form A of cariprazine embonate to solvent was 40 mg/mL. The slurry was stirred for 3 days so cariprazine embonate crystallized to form crystalline form C of cariprazine embonate.

Figure 15:
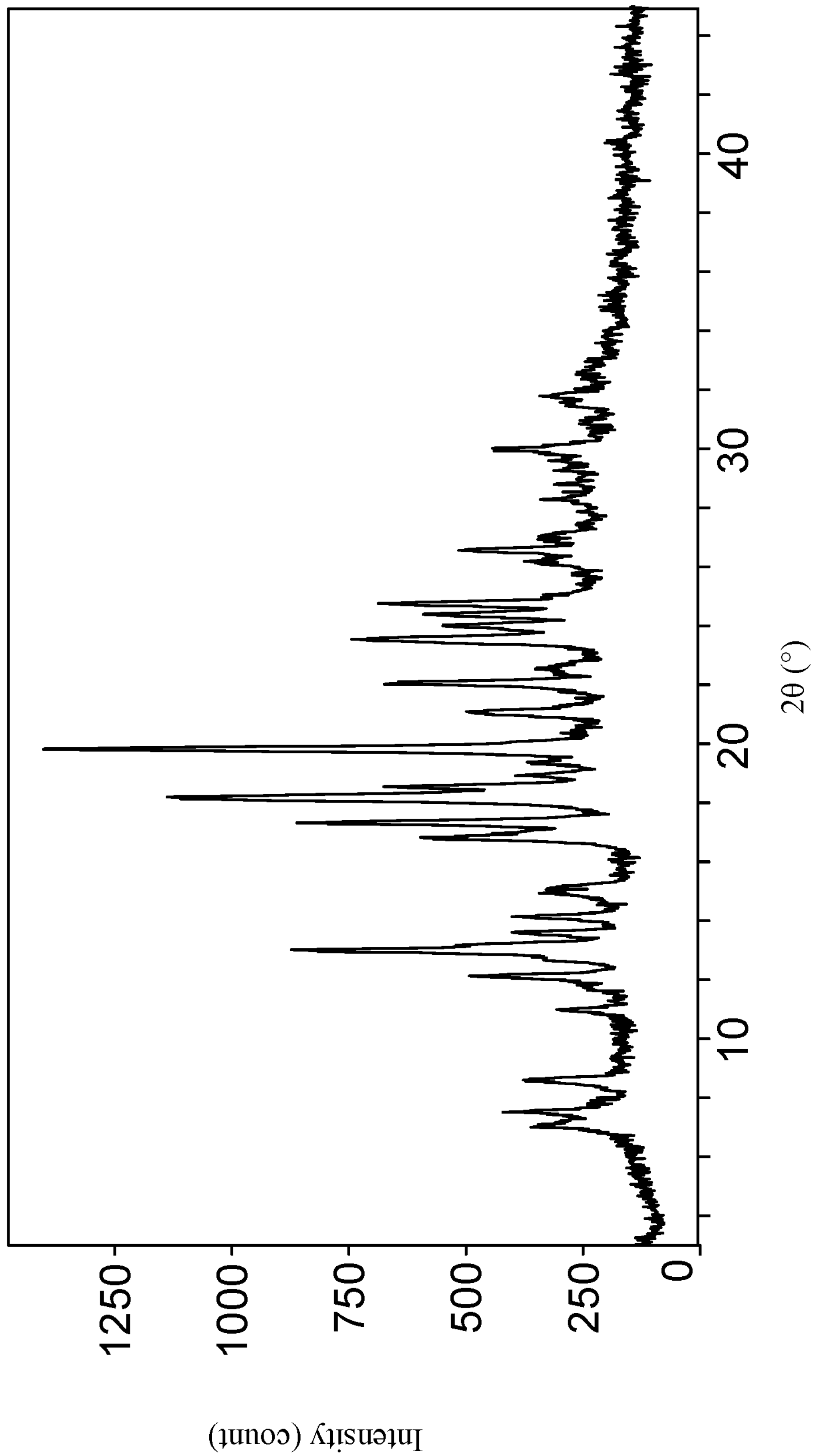
FIG. 15 is an XRPD graph of crystalline form C of cariprazine embonate.

Its X-ray powder diffraction graph is shown in FIG. 15.

Its nuclear magnetic resonance result shows that it was an acetone solvate.

Example 13: Preparation of Crystalline Form D of Cariprazine Embonate 200 mg of the crystalline form A cariprazine embonate prepared in Example 8 was measured out and added to 2 mL of ethanol. The mixture was stirred at room temperature for 48 h to crystallize cariprazine embonate. The solid was collected by filtration and dried in vacuo at 55° C. to give crystalline form D of cariprazine embonate (190 mg, 95% yield).

Figure 10:
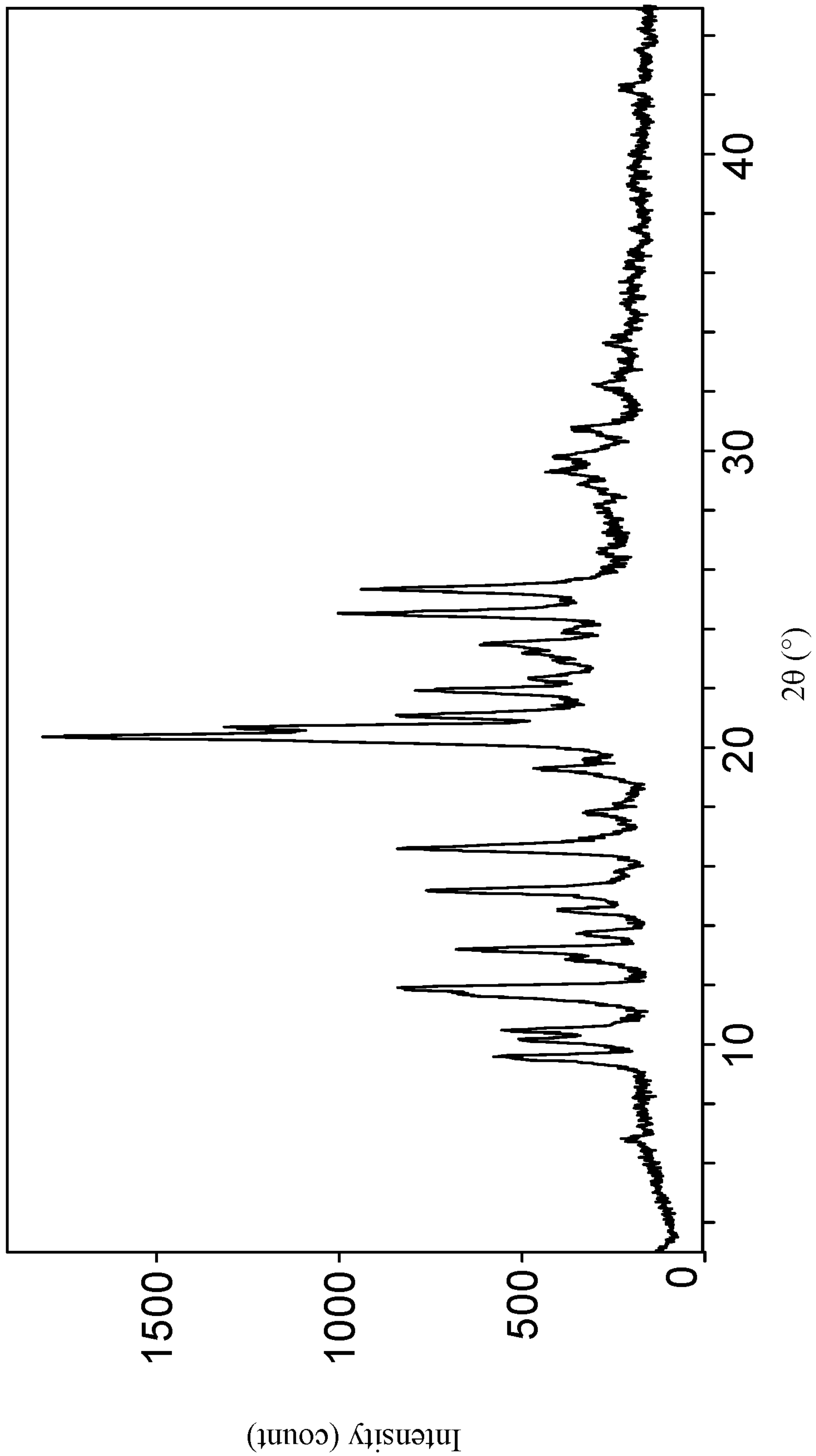
FIG. 10 is an XRPD graph of crystalline form D of cariprazine embonate.

Its X-ray powder diffraction graph is shown in FIG. 10.

Figure 11:
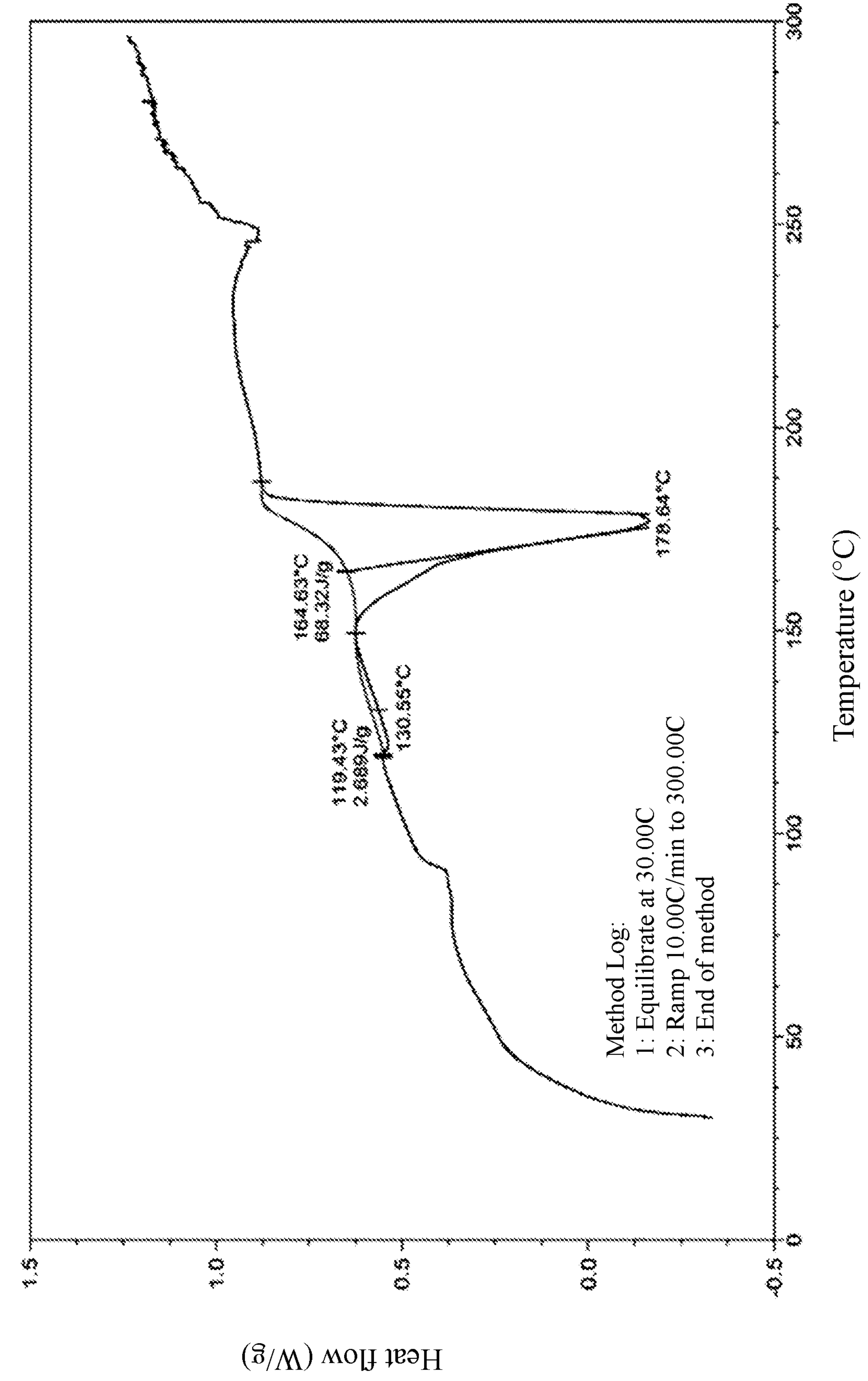
FIG. 11 is a DSC graph of crystalline form D of cariprazine embonate.

Its differential scanning calorimetry graph is shown in FIG. 11, indicating a melting point of 164.6° C.

Figure 12:
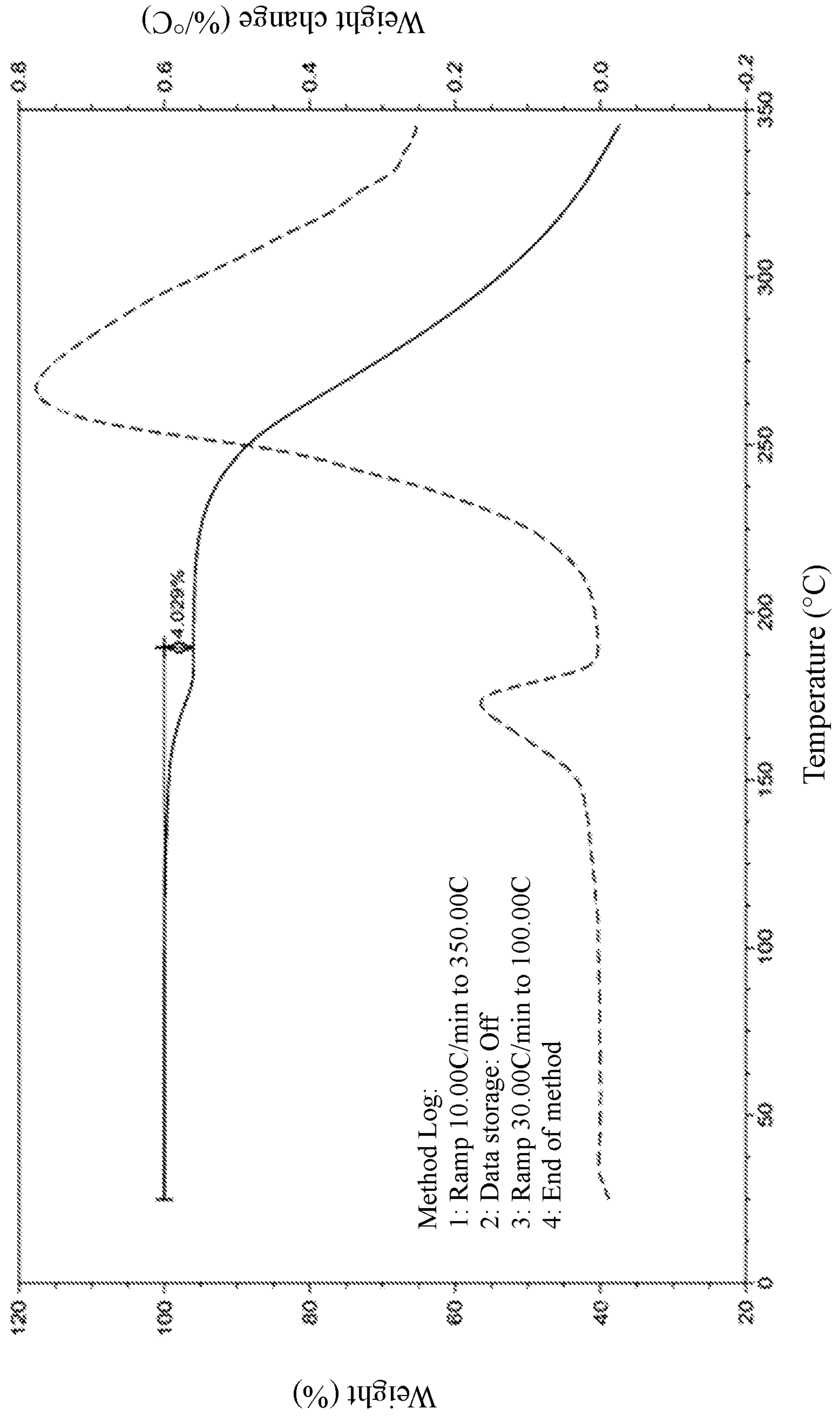
FIG. 12 is a TGA graph of crystalline form D of cariprazine embonate.

Its thermogravimetric analysis graph is shown in FIG. 12, indicating a weight loss of about 4% before 190° C., which is attributed to the loss of water and ethanol.

Figure 13:
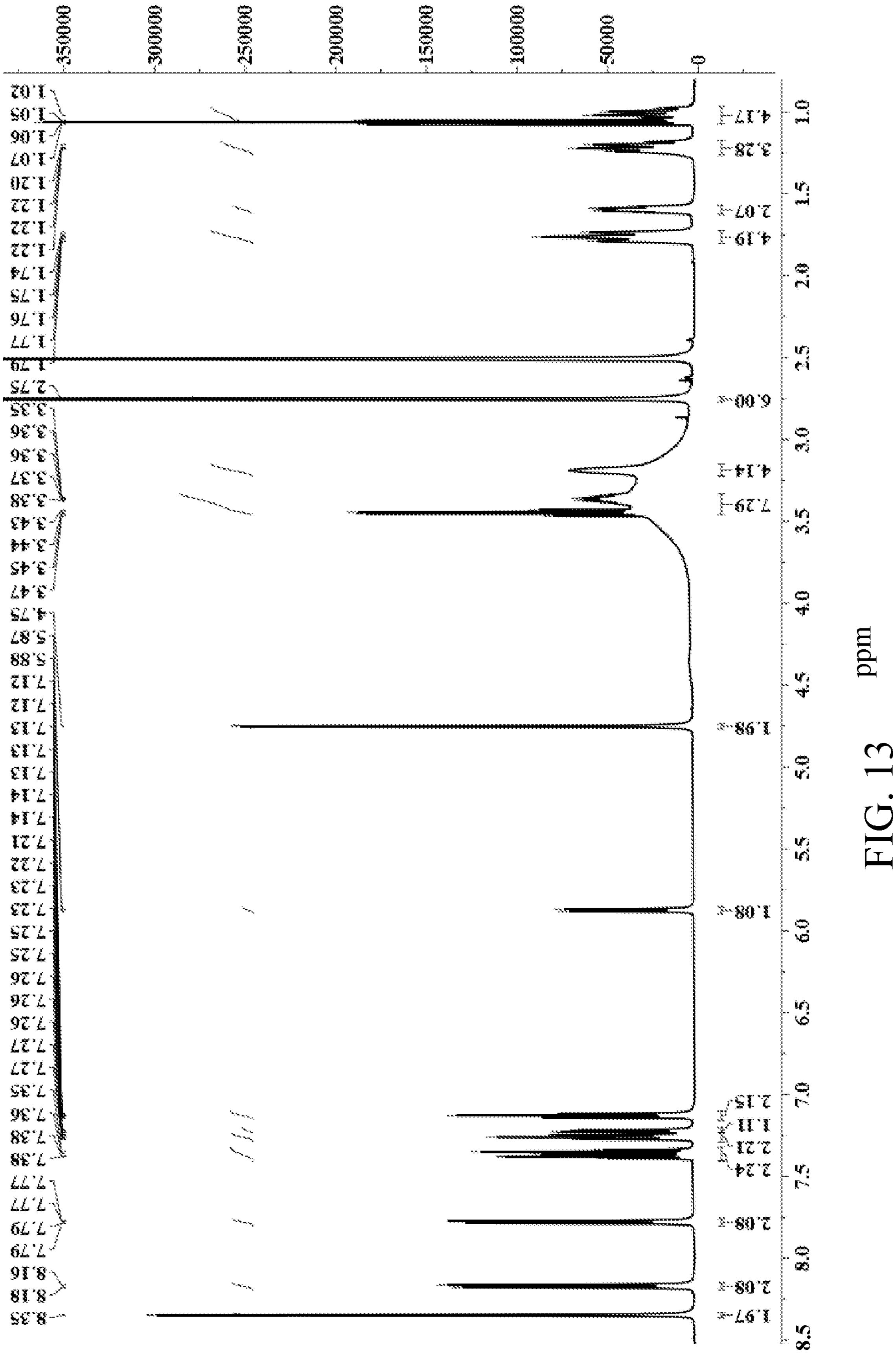
FIG. 13 is a $^1$H-NMR graph of crystalline form D of cariprazine embonate.

Its nuclear magnetic resonance graph is shown in FIG. 13, indicating that cariprazine and embonic acid formed the salt in a molar ratio of 1:1, and the salt contained about 0.67 ethanol molecules.

Example 14: Preparation of Crystalline Form E of Cariprazine Embonate

The crystalline form A of cariprazine embonate obtained in Example 8 was measured out and a slurry of it was formed in acetonitrile solvent. In the slurry, the weight-to-volume ratio of crystalline form A of cariprazine embonate to solvent was 40 mg/mL. The slurry was stirred for 3 days so cariprazine embonate crystallized to form crystalline form E of cariprazine embonate.

Figure 16:
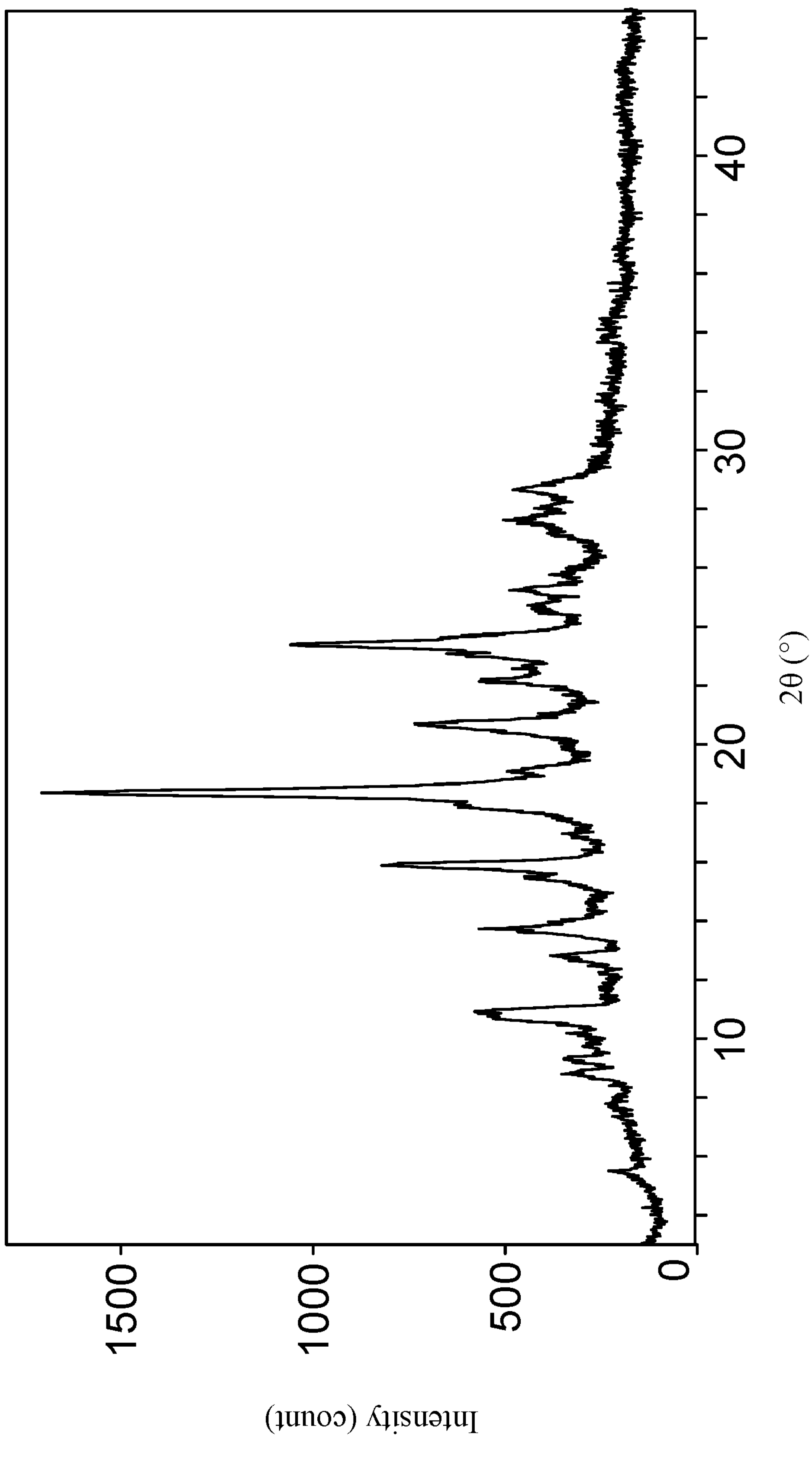
FIG. 16 is an XRPD graph of crystalline form E of cariprazine embonate.

Its X-ray powder diffraction graph is shown in FIG. 16.

Example 15: Preparation of Crystalline Form E of Cariprazine Embonate 2 g of the crystalline form A of cariprazine embonate prepared in Example 9 was measured out and added to 50 mL of acetonitrile. The mixture was stirred at room temperature for 72 h to crystallize cariprazine embonate. The solid was collected by filtration and dried in vacuo at 55° C. to give crystalline form E of cariprazine embonate (1.8 g).

Example 16: Preparation of Crystalline Form F of Cariprazine Embonate 200 mg of the crystalline form A cariprazine embonate prepared in Example 8 was measured out and added to 20 mL of isopropyl acetate. The mixture was stirred at room temperature for 12 h to crystallize cariprazine embonate. The solid was collected by filtration and dried in vacuo at 55° C. to give crystalline form F of cariprazine embonate (180 mg, 90% yield).

Figure 6:
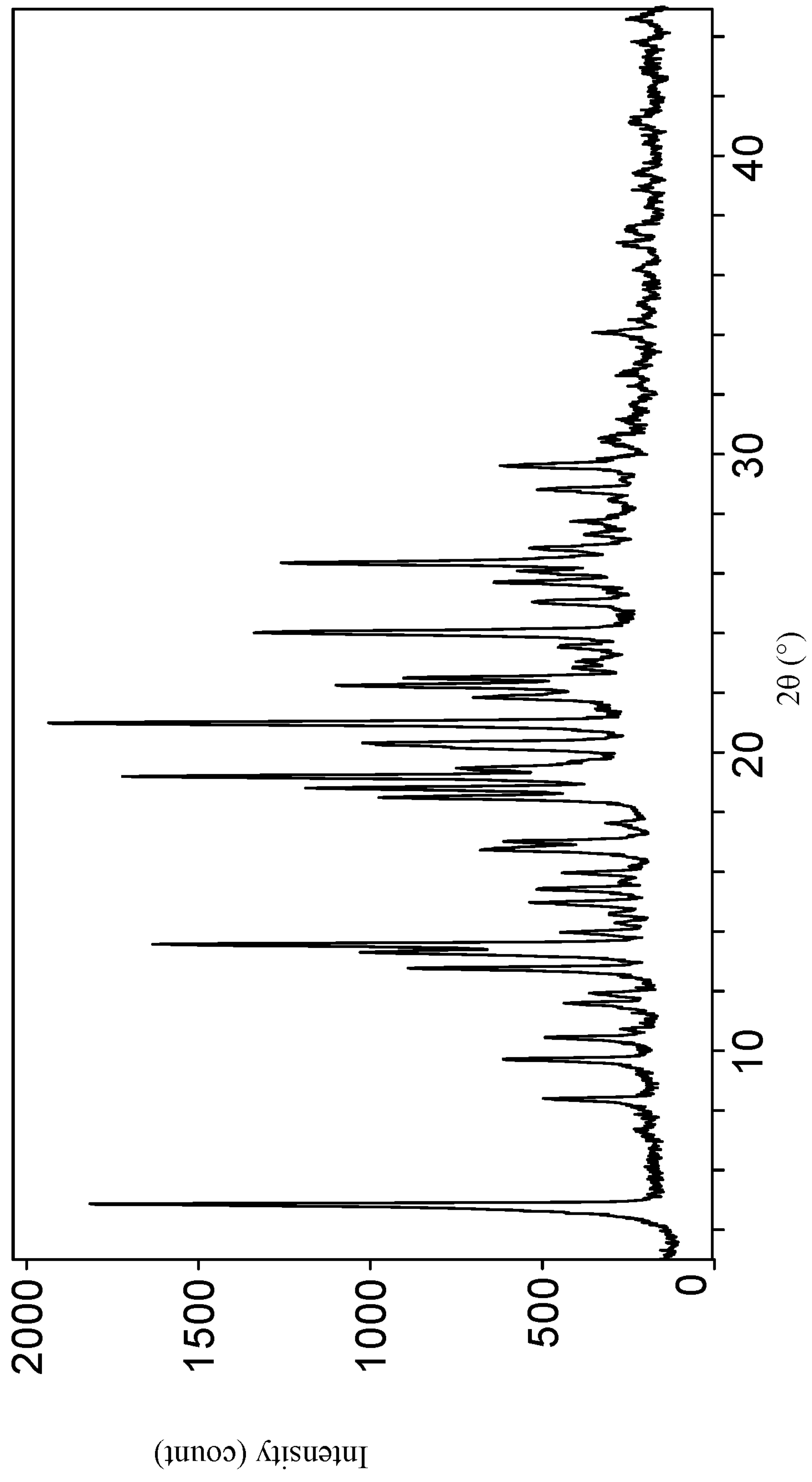
FIG. 6 is an XRPD graph of crystalline form F of cariprazine embonate.

Its X-ray powder diffraction graph is shown in FIG. 6.

Figure 7:
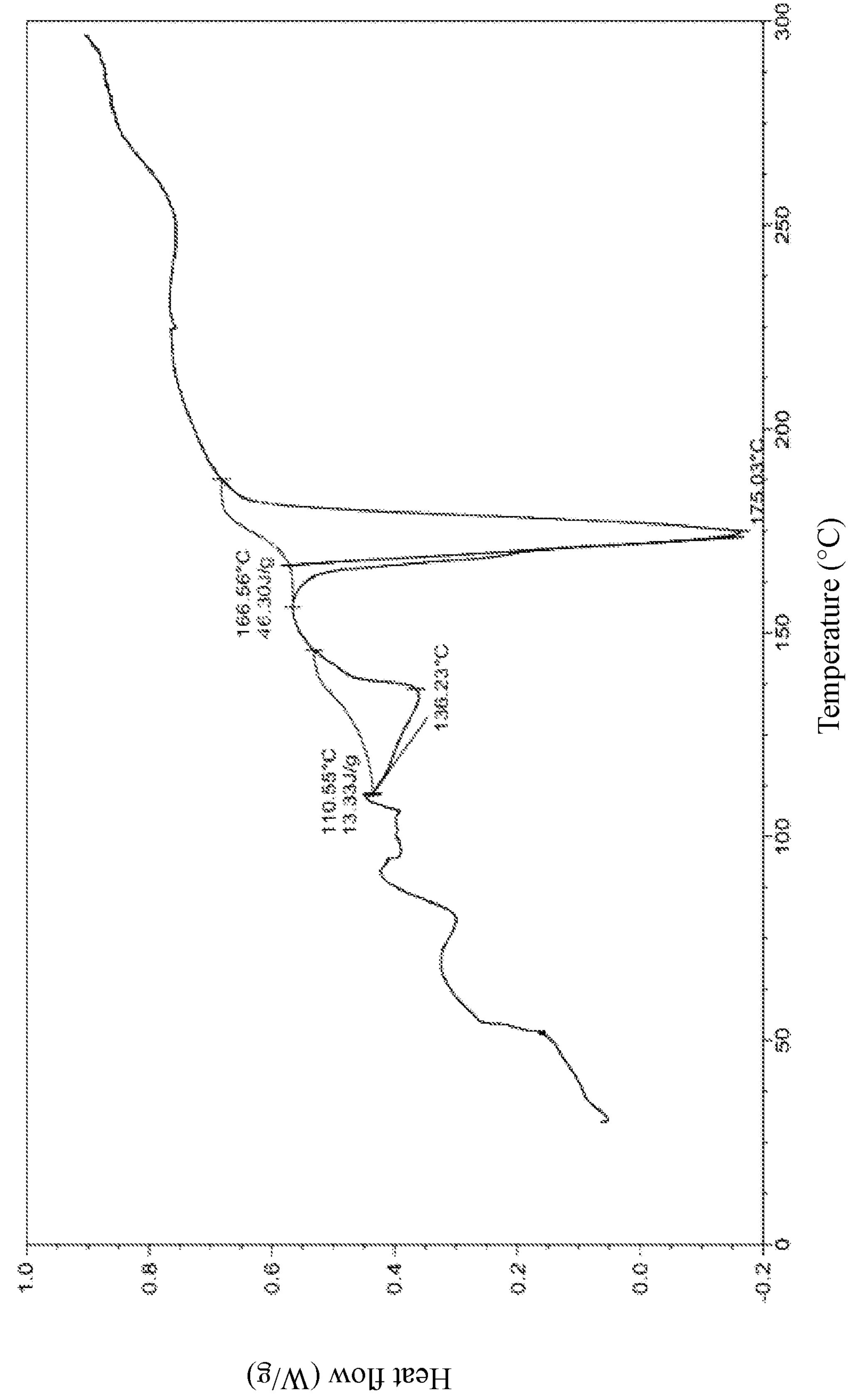
FIG. 7 is a DSC graph of crystalline form F of cariprazine embonate.

Its differential scanning calorimetry graph is shown in FIG. 7, indicating a melting point of about 166.6° C.

Figure 8:
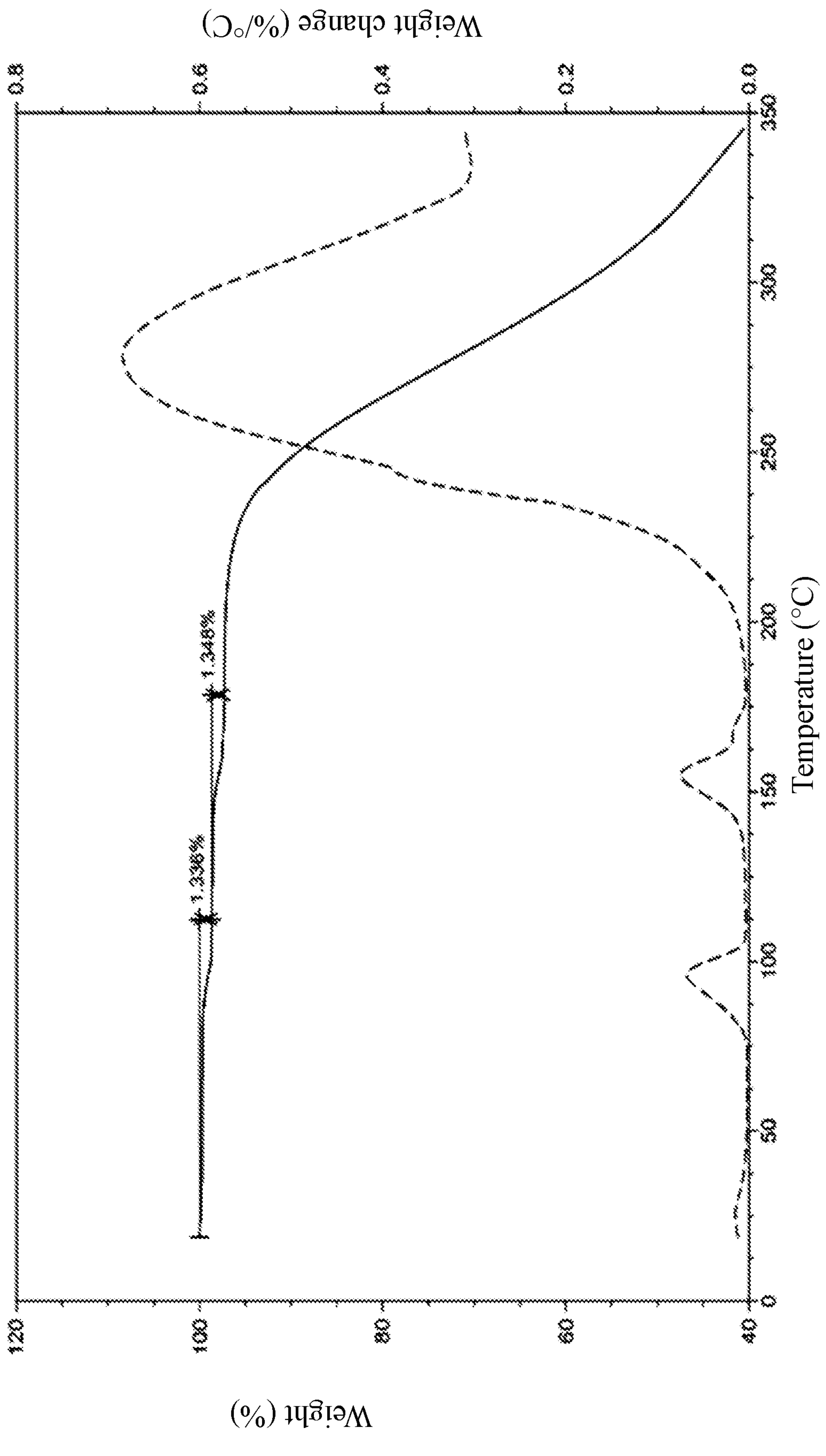
FIG. 8 is a TGA graph of crystalline form F of cariprazine embonate.

Its thermogravimetric analysis graph is shown in FIG. 8, indicating a weight loss of about 1.3% before 115° C., which is attributed to the loss of channel water, and a weight loss of about 1.3% at 115-175° C., which is attributed to the loss of water of crystallization.

Figure 9:
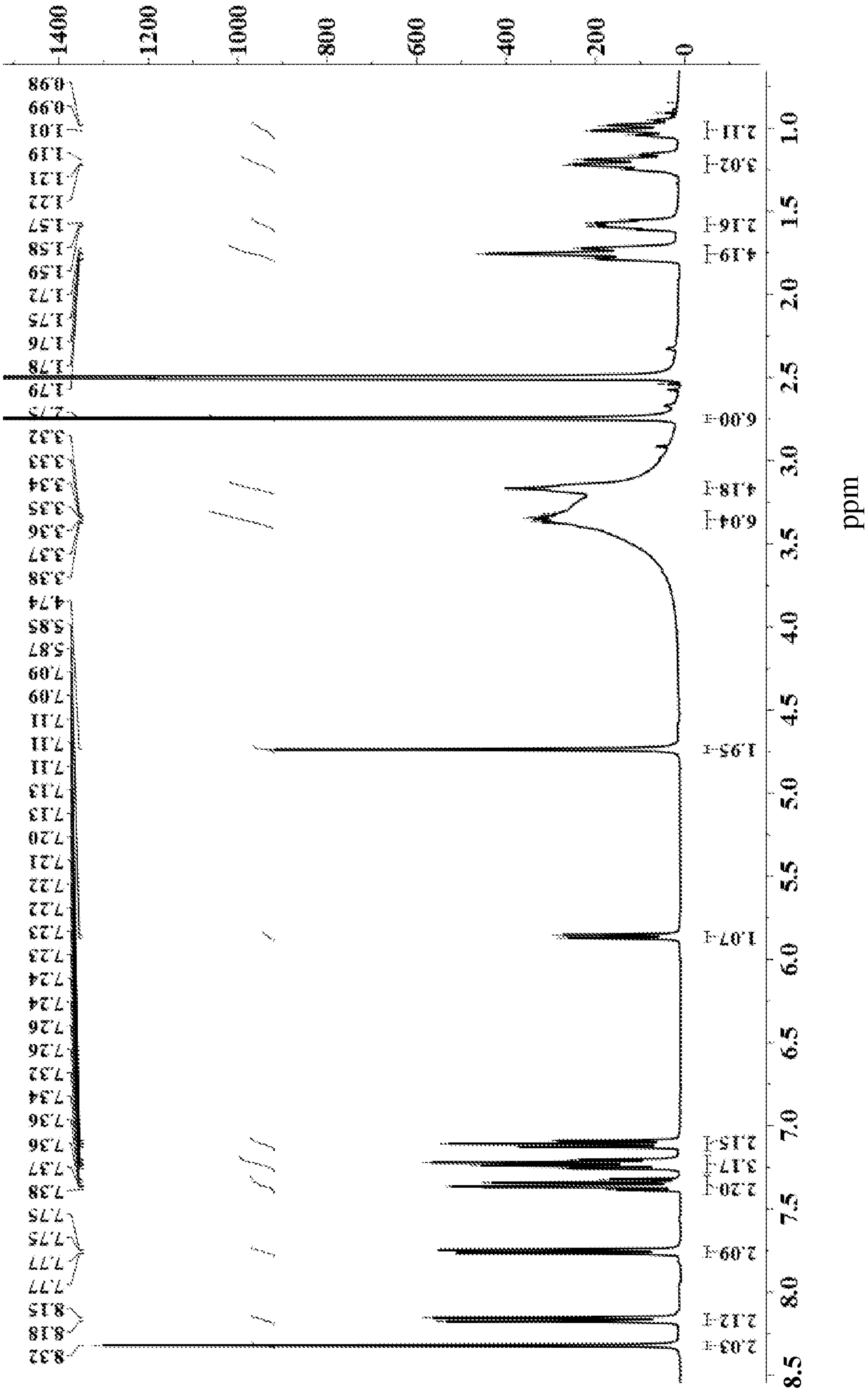
FIG. 9 is a $^1$H-NMR graph of crystalline form F of cariprazine embonate.

Its nuclear magnetic resonance graph is shown in FIG. 9, indicating that cariprazine and embonic acid formed the salt in a molar ratio of 1:1.

Example 17: Preparation of Crystalline Form G of Cariprazine Embonate 200 mg of the crystalline form A of cariprazine embonate obtained in Example 8 was measured out and added to 5 mL of acetonitrile to form a slurry. The slurry was stirred for 5 days so cariprazine embonate crystallized to form crystalline form G of cariprazine embonate.

Figure 17:
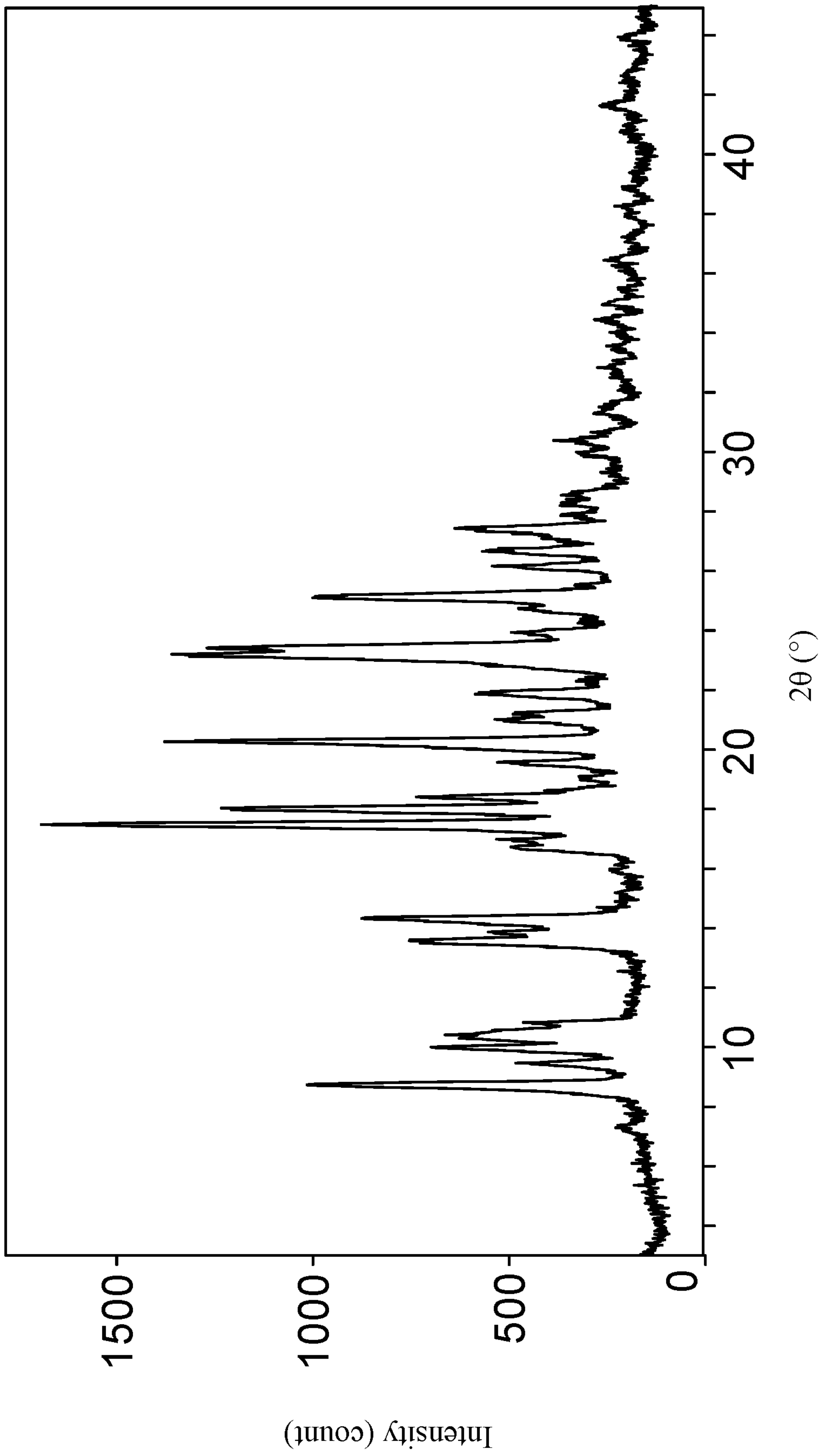
FIG. 17 is an XRPD graph of crystalline form G of cariprazine embonate.

Its X-ray powder diffraction graph is shown in FIG. 17.

Its nuclear magnetic resonance result shows that it was an acetonitrile solvate.

Example 18: Preparation of Crystalline Form I of Cariprazine Embonate

A 15 mg sample of the amorphous solid of cariprazine embonate obtained in Example 1 was measured out and illuminated for 10 days to give crystalline form I of cariprazine embonate.

Figure 18:
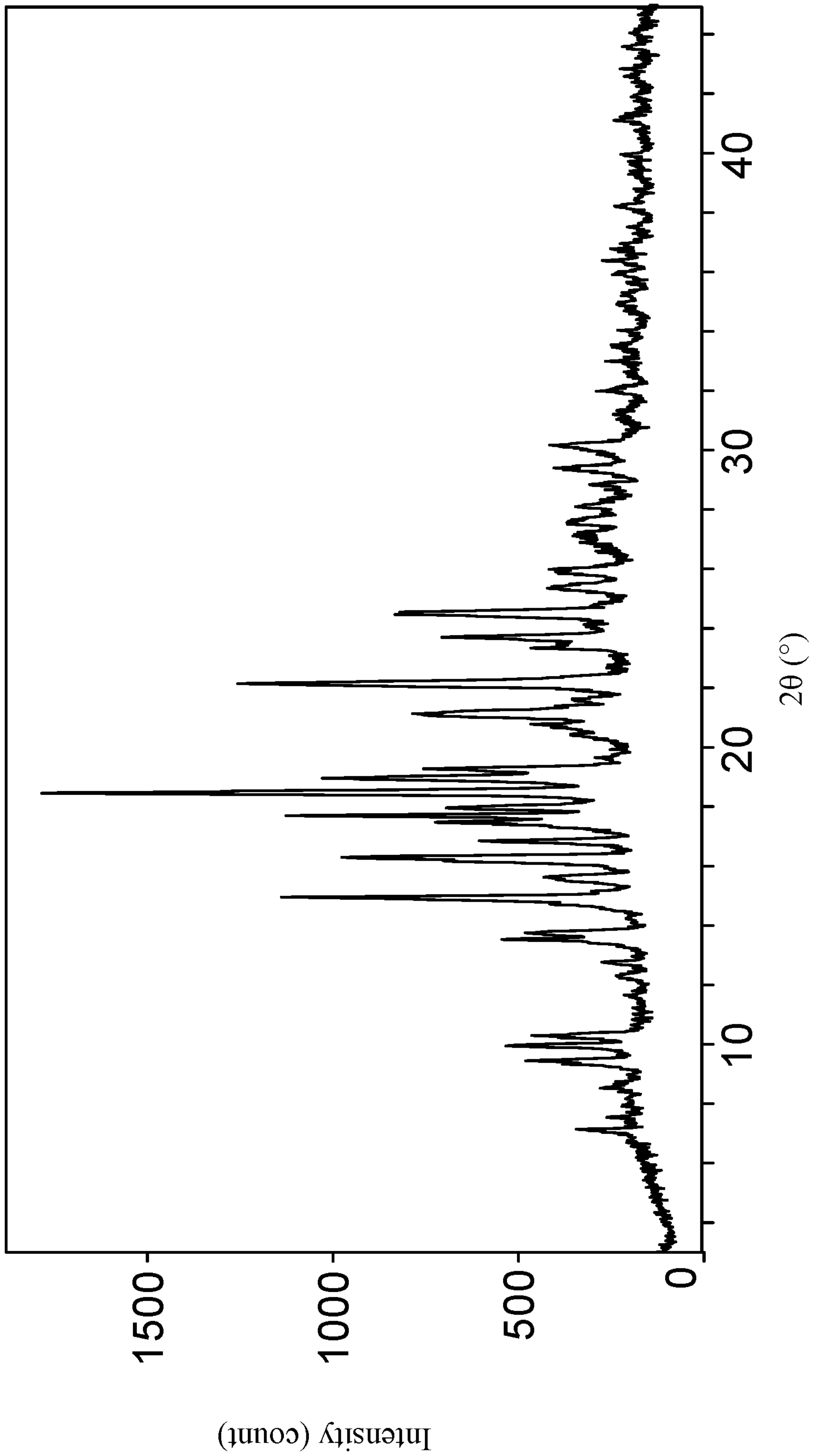
FIG. 18 is an XRPD graph of crystalline form I of cariprazine embonate.

Its X-ray powder diffraction graph is shown in FIG. 18.

Example 19: Preparation of Crystalline Form I of Cariprazine Hydrochloride

Preparation of a sample of crystalline form I of cariprazine hydrochloride according to the original cariprazine hydrochloride patent:

1 g of commercially available cariprazine free base was added to a 25 mL round-bottom flask. 2 mL of methanol and 8 mL of water were added. The mixture was stirred in an oil bath at 70° C. for 0.5 h. A mixed solution of 0.226 mL of concentrated hydrochloric acid and 0.35 mL of water was added. After complete dissolution, the solution was filtered while hot. Heating was stopped and the solution was naturally cooled overnight to give an off-white solid (0.8 g).

Figure 19:
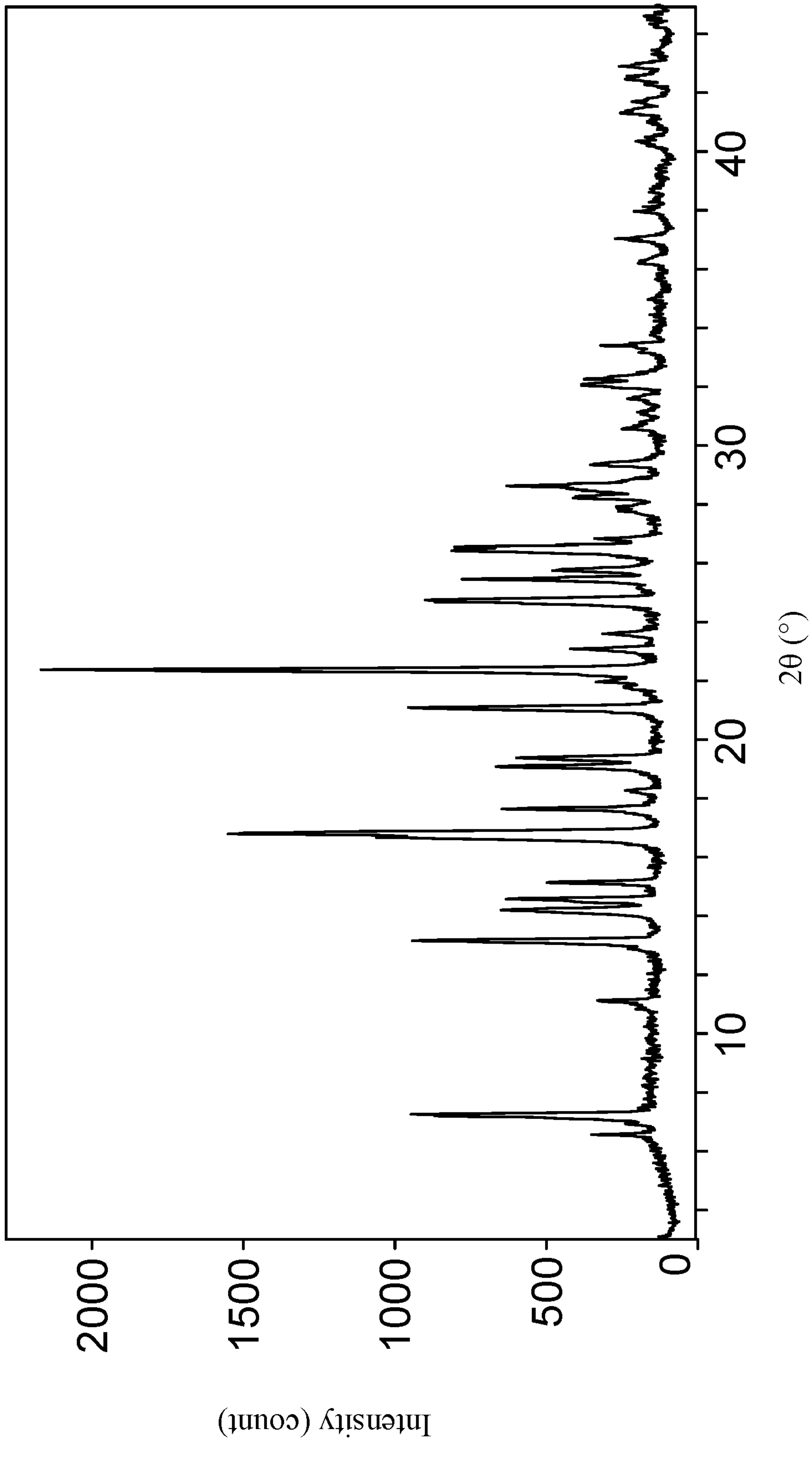
FIG. 19 is an XRPD graph of crystalline form I of cariprazine hydrochloride.

Its X-ray powder diffraction graph is shown in FIG. 19, indicating crystalline form I of cariprazine hydrochloride.

Comparative Example 1: Related Substances and Crystalline Form Stability Comparisons The amorphous cariprazine embonate prepared in Example 1, the crystalline form A of cariprazine embonate prepared in Example 8, the crystalline form B of cariprazine embonate prepared in Example 10, the crystalline form F of cariprazine embonate prepared in Example 16, the crystalline form G of cariprazine embonate prepared in Example 17 and the crystalline form I of cariprazine hydrochloride prepared in Example 19 were left to stand under high-temperature (60° C.) conditions, high-humidity (25° C./90%

RH) conditions, accelerated (40° C./75% RH) conditions and illuminated ($1.2\times10^6$ Lux·h) conditions, and samples were taken on day 0, day 5, day 7 and day 10 and tested by HPLC or XRPD.

The related substances results are shown in Table 1, indicating that the crystalline form A of cariprazine embonate, crystalline form B of cariprazine embonate, crystalline form G of cariprazine embonate and crystalline form A of cariprazine embonate of the present disclosure are relatively stable—the total related substances remained substantially unchanged when they were left to stand under these conditions for 10 days, while amorphous cariprazine embonate was unstable and showed a bigger increase in impurities under high-temperature conditions.

The crystalline form stability results are shown in Table 2, indicating that the crystalline form A of cariprazine embonate of the present disclosure had more excellent crystalline form stability than the crystalline form I of cariprazine hydrochloride that is known—when crystalline form A was left to stand under these conditions for 10 days, its crystalline form did not change and its crystallinity also did not change significantly; and that the crystalline form F of cariprazine embonate of the present disclosure was relatively stable under high-temperature conditions and illuminated conditions—its crystalline form did not change—and would change into crystalline form A of cariprazine embonate under high-humidity conditions and accelerated conditions.

TABLE 1

Related substances results

| Name | Time | Changes (%) in total related substances relative to day 0 | | | |
|---|---|---|---|---|---|
| | | High temperature | High humidity | Illuminated | Accelerated |
| Crystalline form I of cariprazine hydrochloride | 0 days | | 0 | | |
| | 5 days | −0.01 | −0.03 | 0.02 | 0.01 |
| | 10 days | −0.04 | −0.03 | 0.02 | 0 |
| Crystalline form A of cariprazine embonate | 0 days | | 0 | | |
| | 5 days | 0.03 | −0.03 | −0.02 | −0.01 |
| | 10 days | 0.05 | −0.02 | −0.03 | −0.03 |
| Crystalline form B of cariprazine embonate | 0 days | | 0 | | |
| | 5 days | 0.01 | 0.01 | 0.01 | 0.01 |
| | 10 days | 0.03 | 0.03 | 0.03 | 0.03 |
| Crystalline form G of cariprazine embonate | 0 days | | 0 | | |
| | 5 days | 0.13 | 0.01 | 0.06 | 0.07 |
| | 10 days | 0.13 | 0.12 | −0.01 | 0.08 |
| Amorphous cariprazine embonate | 0 days | | 0 | | |
| | 5 days | 0.61 | −0.04 | 0.44 | −0.07 |
| | 10 days | 0.83 | −0.05 | 0.31 | 0.11 |

TABLE 2

Crystalline form stability results

| Name | Time | Crystalline form results | | | |
|---|---|---|---|---|---|
| | | High temperature | High humidity | Illuminated | Accelerated |
| Crystalline form A of cariprazine embonate | 10 days | Crystalline form did not change | Crystalline form did not change | Crystalline form did not change | Crystalline form did not change |
| Crystalline form I of cariprazine hydrochloride | 10 days | Crystalline form did not change | Crystalline form did not change | Crystalline form did not change | Crystallinity decreased |
| Crystalline form F of cariprazine embonate | 7 days | Crystalline form did not change | Crystalline forms A + F | Crystalline form did not change | Crystalline forms A + F |

Comparative Example 2: Solubility Comparison

The amorphous cariprazine embonate prepared in Example 1, the amorphous cariprazine hemiembonate prepared in Example 3, the amorphous cariprazine laurate prepared in Example 5, the cariprazine palmitate prepared in Example 6, the cariprazine sebacate, cariprazine succinate, cariprazine malate, cariprazine lactate, cariprazine undecanoate and cariprazine heptanoate prepared in Example 7, the crystalline form A of cariprazine embonate prepared in Example 8, the crystalline form B of cariprazine embonate prepared in Example 10, the crystalline form F of cariprazine embonate prepared in Example 16, the crystalline form G of cariprazine embonate prepared in Example 17, the crystalline form I of cariprazine hydrochloride prepared in Example 19 and cariprazine were each added to a corresponding medium. The mixtures were shaken at 37° C. for 24 h and filtered through 0.45 μm aqueous-phase filter membranes. The filtrates were collected and the solubility was determined by high performance liquid chromatography. pH3, pH4, pH5 and pH6 represent acetate buffer solutions, and pH7, pH7.4, pH8 and pH9 represent phosphate buffer solutions.

The results are shown in Table 3, indicating that the solubilities of the cariprazine embonate and crystalline forms thereof and cariprazine hemiembonate prepared in the present disclosure were all significantly lower—the solubility of cariprazine embonate in water was 3-10 μg/mL, which is equivalent to one eighteenth to one sixtieth of the cariprazine's solubility (about 180 μg/mL) and one thousandth to one thirty-six hundredth of the cariprazine hydrochloride's solubility (about 11 mg/mL)—and were all relatively low in media having different pH values. As they have sustained-release effects, their equivalent solubilities in media having different pH values enable the rate of release to be least dependent on pH, so that influence on their rates of drug release in pH environments of different areas in the body is avoided, burst releases or excessive plasma concentrations in local areas in the body are avoided, and the difference in drug release between individuals is reduced. In addition, as cariprazine embonate has relatively good crystalline form stability, it is suitable for use in long-acting preparations so fewer doses can be used and therefore patient compliance is improved. Cariprazine embonate has a good marketing prospect.

TABLE 3

| Solubility results | | | | | | | | |
|---|---|---|---|---|---|---|---|---|
| | Solubility (μg/mL) | | | | | | | |
| Sample | pH 3 | pH 4 | pH 5 | pH 6 | Water | pH 7 | pH 8 | pH 9 |
| Cariprazine | 1363.4 | / | 242.7 | / | 179.9 | 3.2 | / | 1.4 |
| Cariprazine hydrochloride | 12302.5 | 9765.9 | 10814. | / | 10935.1 | / | / | / |
| Amorphous cariprazine hemiembonate | 92.8 | / | 30.4 | / | 28.0 | 17.6 | / | 1.5 |
| Amorphous cariprazine embonate | 151.2 | 19.1 | 17.7 | 19.0 | 10.4 | 18.8 | 4.6 | 4.2 |
| Crystalline form A of cariprazine embonate | 23.7 | 1.8 | 4.9 | 15.0 | 3.2 | 31.9 | 5.9 | 7.6 |
| Crystalline form B of cariprazine embonate | 34.9 | 5.5 | 5.2 | 17.6 | 3.2 | 32.0 | 7.0 | 7.8 |
| Crystalline form G of cariprazine embonate | 147.6 | 16.9 | 16.5 | 17.5 | 7.6 | 20.3 | 5.9 | 9.9 |
| Crystalline form F of cariprazine embonate | / | 7.2 | 5.1 | 10.8 | 2.9 | 27.1 | 0.21 | / |
| Cariprazine undecanoate | 466.0 | / | 211.5 | / | 72.5 | 6.7 | / | 6.7 |
| Cariprazine heptanoate | 385.5 | / | 155.1 | / | 42.5 | 3.4 | / | 0.5 |
| Cariprazine laurate | 390.8 | / | 174.4 | / | 37.2 | 3.5 | / | 0.4 |
| Cariprazine palmitate | 222.7 | / | 196.3 | / | 5.8 | 3.4 | / | 0.2 |
| Cariprazine sebacate | >152.7 | / | <169.7 | / | >169.7 | <152.7 | / | <186.7 |
| Cariprazine succinate | >215.5 | / | >195.9 | / | >261.2 | >195.9 | / | <215.5 |
| Cariprazine malate | >266.4 | / | >228.4 | / | >1065.7 | <304.5 | / | <152.2 |
| Cariprazine lactate | <227.1 | / | <268.4 | / | >309.7 | <247.8 | / | <206.5 |

Comparative Example 3: In Vitro Dissolution Simulation Experiment

Figure 20:
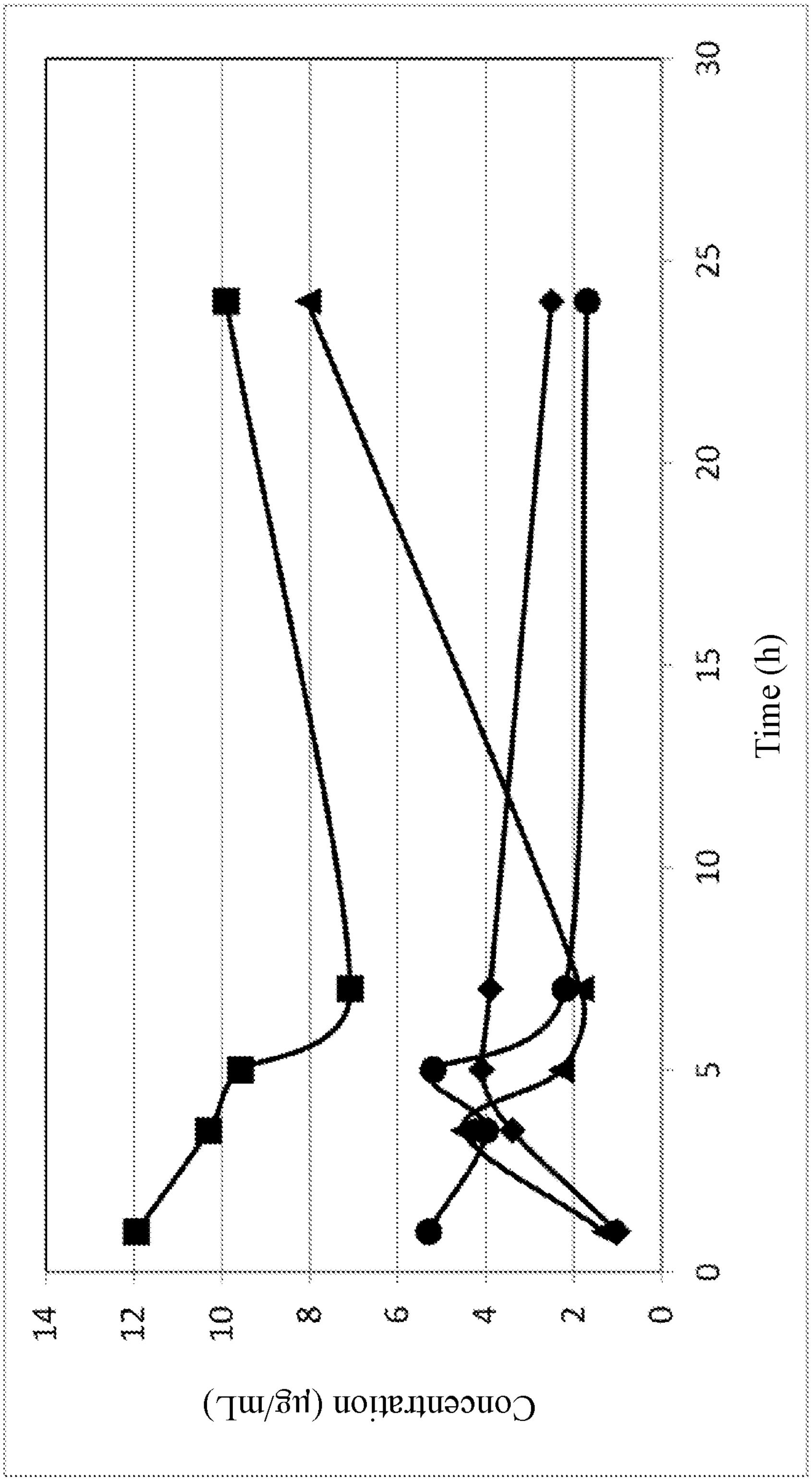
FIG. 20 is a graph showing the results of in vitro dissolution simulation experiments (■ for amorphous cariprazine embonate; ♦ for crystalline form A of cariprazine embonate; ● for crystalline form B of cariprazine embonate; and ▲ for crystalline form G of cariprazine embonate)

The amorphous cariprazine embonate prepared in Example 1, the crystalline form A of cariprazine embonate prepared in Example 8, the crystalline form B of cariprazine embonate prepared in Example 10 and the crystalline form G of cariprazine embonate prepared in Example 17 were each added to a phosphate buffer solution medium having a pH of 7.4. The mixtures were shaken at 37° C. Point samples were taken at 1 h, 3 h, 5 h, 7 h and 24 h and the solubility was determined. The results are shown in Table 4 and FIG. 20, indicating that the compound samples of both the crystalline form A of cariprazine embonate and crystalline form B of cariprazine embonate prepared in the present disclosure dissolved more gently at pH 7.4 than the amorphous sample of cariprazine embonate and had a small 24-h solubility, which indicates that compounds in crystalline form are more suitable for use as pharmaceutically acceptable salts to avoid excessive plasma concentrations.

TABLE 4

| Results of the in vitro dissolution simulation experiment | | | | | |
|---|---|---|---|---|---|
| | Concentration (μg/mL) | | | | |
| Sample | 1 (h) | 3.5 (h) | 5 (h) | 7 (h) | 24 (h) |
| Crystalline form A of cariprazine embonate | 1.0 | 3.4 | 4.1 | 3.9 | 2.5 |
| Crystalline form B of cariprazine embonate | 5.3 | 4.0 | 5.2 | 2.2 | 1.7 |

TABLE 4-continued

| Results of the in vitro dissolution simulation experiment | | | | | |
|---|---|---|---|---|---|
| | Concentration (μg/mL) | | | | |
| Sample | 1 (h) | 3.5 (h) | 5 (h) | 7 (h) | 24 (h) |
| Crystalline form G of cariprazine embonate | 1.30 | 4.51 | 2.28 | 1.84 | 8.05 |
| Amorphous cariprazine embonate | 11.94 | 10.3 | 9.58 | 7.08 | 9.9 |

Comparative Example 4: Solution Stability Comparison

Figure 21:
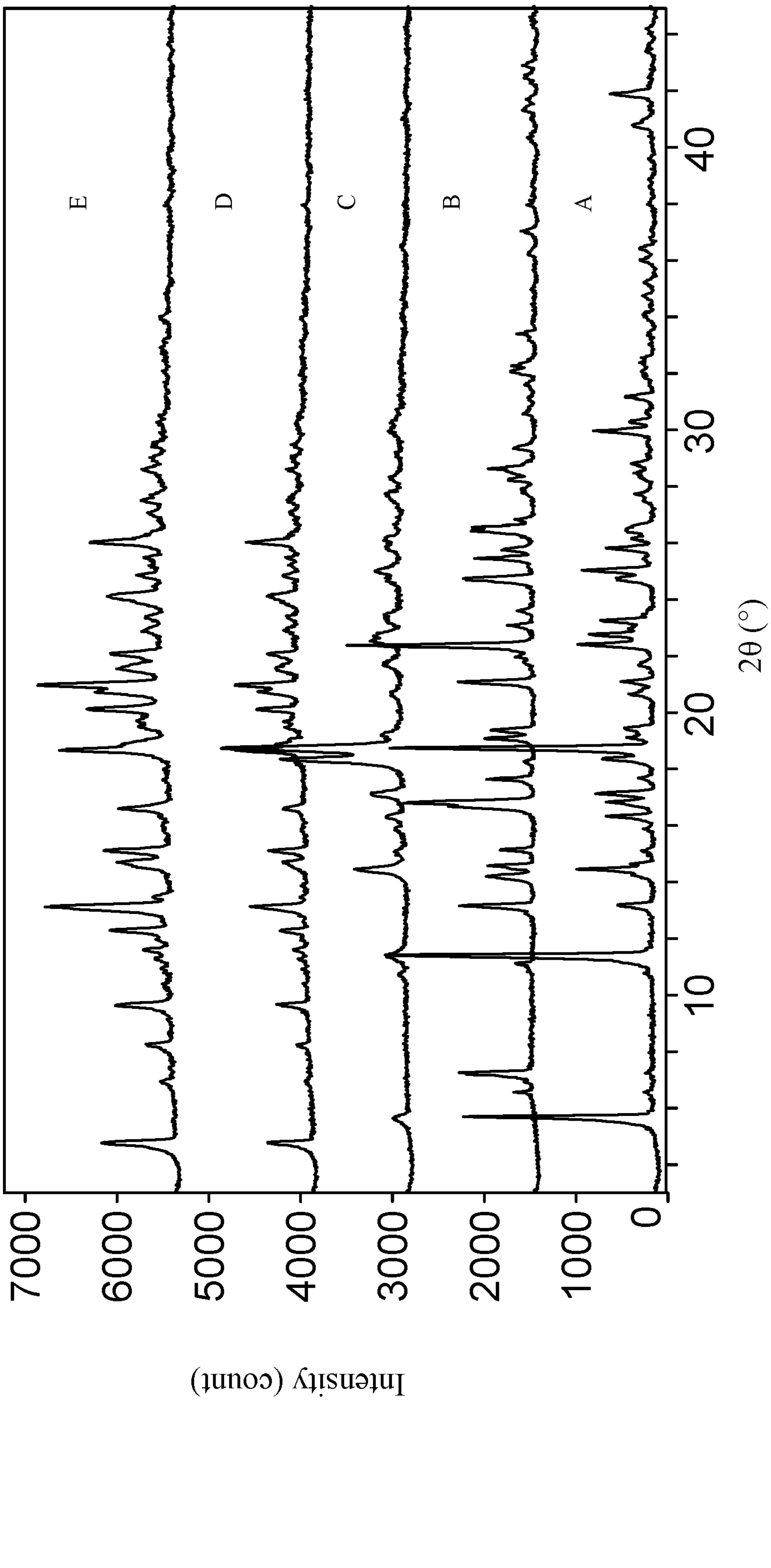
FIG. 21 is an overlay of XRPD graphs of cariprazine embonate and cariprazine hydrochloride at pH 7.4 in Comparative Example 4 (A for cariprazine free base; B for crystalline form I of cariprazine hydrochloride; C for crystalline form I of cariprazine hydrochloride that has been shaken in a pH 7.4 medium; D for crystalline form A of cariprazine embonate; and E for crystalline form A of cariprazine embonate that has been shaken in a pH 7.4 medium)

The crystalline form A of cariprazine embonate prepared in Example 8 and the crystalline form I of cariprazine hydrochloride prepared in Example 19 were each added to corresponding media such as pH6, pH7, pH7.4, pH8, pH9, etc. The mixtures were shaken at 37° C. for 4 h and centrifuged. The residues were tested by XRPD, and the results show that crystalline form A of cariprazine embonate did not change while crystalline form I of cariprazine hydrochloride dissociated into cariprazine free base. The pH7.4 comparison results are shown in FIG. 21 (others not shown). As can be seen from the results, crystalline form A of cariprazine embonate is more stable in solution than crystalline form I of cariprazine hydrochloride and therefore can effectively avoid efficacy change caused by crystalline form change after administration so medication safety is improved.

Examples 20-25: Aqueous Suspensions of Cariprazine Embonate with Different Amounts of Suspending Agent

| Component | Amount (mg) Example 20 | Example 21 | Example 22 | Example 23 | Example 24 | Example 25 |
|---|---|---|---|---|---|---|
| Crystalline form A of cariprazine embonate (Example 8 or Example 9) | | | 573 | | | |
| Tween 20 | | | 100 | | | |
| Disodium phosphate | | | 45 | | | |
| Monosodium phosphate | | | 9 | | | |
| Mannitol | | | 247 | | | |
| Sodium carboxymethylcellulose | 15 | 25 | 35 | 50 | 75 | 100 |
| Aqueous solution of sodium hydroxide (1N) | | | Proper amount | | | |
| Aqueous solution of hydrochloric acid (1N) | | | Proper amount | | | |
| Water for injection | | | qs 10.0 mL | | | |

Preparation Process (1) The formula amounts of tween 20, disodium phosphate, monosodium phosphate and mannitol were measured out, added to water for injection that was about 60% of the total amount of the preparation, and dissolved and dispersed by stirring.

(2) The formula amount of crystalline form A of cariprazine embonate was added to obtain aqueous suspensions of coarse particles.

(3) The aqueous suspensions of coarse particles described above were ground with a ball mill to obtain suspensions having Dv(90) of less than or equal to 10 microns.

(4) The formula amounts of sodium carboxymethylcellulose were added to the suspensions described above and completely dispersed by stirring. Optionally, the pH was adjusted to 4.0-9.0 with sodium hydroxide or hydrochloric acid. The suspensions were brought to volume to obtain suspensions of Examples 20-25.

The syringeability, suspendibility, settling ratio and redispersibility of the formula samples prepared in Examples 20-25 were investigated, and the investigation revealed that the suspension samples described above could all pass through 0.45×15 mm syringe needles and had good suspendibility, and that the samples of Examples 22-25 had good 24-hour settling ratios and redispersibility.

Examples 26-30: Aqueous Suspensions of Cariprazine Embonate with Different Amounts of Wetting Agent

| Component | Amount (mg) Example 26 | Example 27 | Example 28 | Example 29 | Example 30 |
|---|---|---|---|---|---|
| Cariprazine embonate Crystalline form A (Example 8 or Example 9) | | | 573 | | |
| Tween 20 | 10 | 25 | 50 | 75 | 100 |
| Disodium phosphate | | | 45 | | |
| Monosodium phosphate | | | 9 | | |
| Mannitol | | | 247 | | |
| Sodium carboxymethylcellulose | | | 50 | | |
| Aqueous solution of sodium hydroxide (1N) | | | Proper amount | | |
| Aqueous solution of hydrochloric acid (1N) | | | Proper amount | | |
| Water for injection | | | qs 10.0 mL | | |

Preparation Process (1) The formula amounts of tween 20, disodium phosphate, monosodium phosphate and mannitol were measured out, added to water for injection that was about 60% of the total amount of the preparation, and dissolved and dispersed by stirring.

(2) The formula amount of crystalline form A of cariprazine embonate was added to obtain aqueous suspensions of coarse particles.

(3) The aqueous suspensions of coarse particles described above were ground with a ball mill to obtain suspensions having Dv(90) of less than or equal to 10 microns.

(4) The formula amount of sodium carboxymethylcellulose was added to the suspensions described above and completely dispersed by stirring. Optionally, the pH was adjusted to 4.0-9.0 with sodium hydroxide or hydrochloric acid. The suspensions were brought to volume to obtain suspensions of Examples 26-30.

The syringeability, suspendibility, settling ratio and wettability of the formula samples prepared in Examples 26-30 were investigated, and the investigation revealed that the suspension samples described above could all pass through 0.45×15 mm syringe needles and had good suspendibility, settling ratios and wettability.

Examples 31-34: Aqueous Suspensions of Cariprazine Embonate of Different Particle Sizes

| | Amount (mg) |
|---|---|
| Component | Example 31/Example 32/Example 33/Example 34 |
| Cariprazine embonate Crystalline form A (Example 8 or Example 9) | 573 |
| Tween 20 | 100 |
| Disodium phosphate | 45 |
| Monosodium phosphate | 9 |
| Mannitol | 247 |
| Sodium carboxy-methylcellulose | 50 |
| Water for injection | qs 10.0 mL |

Preparation Process (1) The formula amounts of tween 20, disodium phosphate, monosodium phosphate and mannitol were measured out, added to water for injection that was about 60% of the total amount of the preparation, and dissolved and dispersed by stirring.

(2) The formula amount of crystalline form A of cariprazine embonate was added to obtain aqueous suspensions of coarse particles.

(3) The aqueous suspensions of coarse particles obtained above in Examples 31-34 were ground and dispersed with a ball mill.

(4) The formula amount of sodium carboxymethylcellulose was added to the suspensions described above and completely dispersed by stirring. The suspensions were brought to volume to obtain suspensions of Examples 32-35 having a pH of 7.4±0.2.

(5) The particle size distribution of the ground example samples was measured on an OMEC LS-909 particle size analyzer, and the results are shown in the table below.

| Example | Dv10(μm) | Dv50(μm) | Dv90(μm) |
|---|---|---|---|
| Example 31 | 9.338 | 27.446 | 79.618 |
| Example 32 | 1.257 | 4.794 | 14.601 |
| Example 33 | 0.714 | 1.747 | 4.635 |
| Example 34 | 0.715 | 1.097 | 2.097 |

From the results in the table above, it can be seen that in aqueous suspensions of the same formula, aqueous suspensions of particles of different particle sizes (Dv90) can be prepared by controlling the grinding parameters.

Examples 35-37: Aqueous Suspensions of Different Crystalline Forms of Cariprazine Embonate

| | Amount (mg) | | |
|---|---|---|---|
| Name | Example 35 | Example 36 | Example 37 |
| Cariprazine embonate in amorphous form (Example 2) | 573 | — | — |
| Cariprazine embonate in crystalline form B (Example 11) | — | 573 | — |
| Cariprazine embonate in crystalline form E (Example 15) | — | — | 573 |
| Tween 20 | 100 | 100 | 100 |
| Disodium phosphate | 45 | 45 | 45 |
| Monosodium phosphate | 9 | 9 | 9 |
| Mannitol | 247 | 247 | 247 |
| Sodium carboxymethylcellulose | 50 | 50 | 50 |

Preparation Process (1) The formula amounts of tween 20, disodium phosphate, monosodium phosphate and mannitol were measured out, added to water for injection that was about 60% of the total amount of the preparation, and dissolved and dispersed by stirring.

(2) The formula amounts of corresponding samples of cariprazine embonate were added to obtain aqueous suspensions of coarse particles.

(3) The aqueous suspensions of coarse particles obtained above in Examples 35-37 were ground and dispersed with a ball mill.

(4) The formula amount of sodium carboxymethylcellulose was added to the suspensions described above and completely dispersed by stirring. The suspensions were brought to volume to obtain suspensions of Examples 35-37 having a pH of 7.4±0.2.

(5) The particle size distribution of the ground example samples was measured on an OMEC LS-909 particle size analyzer, and the results are shown in the table below.

| Example | Dv10(μm) | Dv50(μm) | Dv90(μm) |
|---|---|---|---|
| Example 35 | 0.833 | 2.684 | 6.825 |
| Example 36 | 0.880 | 2.652 | 5.613 |
| Example 37 | 0.879 | 2.586 | 5.867 |

The syringeability, suspendibility, settling ratio and wettability of the formula samples prepared in Examples 35-37 were investigated, and the investigation revealed that the suspension samples described above could all pass through 0.45×15 mm syringe needles and had good suspendibility, settling ratios and wettability.

According to the results in the table above and the investigation of syringeability, suspendibility, settling ratio and wettability, aqueous suspensions of the same formula and the same grinding parameters apply to different crystalline forms of cariprazine embonate.

Example 38: Aqueous Suspension of Cariprazine Hydrochloride

| Component | Amount (mg) Example 38 |
|---|---|
| Cariprazine hydrochloride | 326 |
| Tween 20 | 100 |
| Disodium phosphate | 45 |
| Monosodium phosphate | 9 |

-continued

| Component | Amount (mg) Example 38 |
|---|---|
| Mannitol | 247 |
| Sodium carboxymethylcellulose | 50 |
| Water for injection | qs 10.0 mL |

Preparation Process (1) The formula amounts of tween 20, disodium phosphate, monosodium phosphate and mannitol were measured out, added to water for injection that was about 60% of the total amount of the preparation, and dissolved and dispersed by stirring.

(2) The formula amount of cariprazine hydrochloride was added to obtain an aqueous suspension of coarse particles.

(3) The aqueous suspension of coarse particles obtained above was ground and dispersed with a ball mill.

(4) The formula amount of sodium carboxymethylcellulose was added to the suspension described above and completely dispersed by stirring. The suspension was brought to volume to obtain a suspension of Examples 38 having a pH of 7.4±0.2.

(5) The particle size distribution of the ground example sample was measured on an OMEC LS-909 particle size analyzer, and the results are shown in the table below.

| Example | Dv10(μm) | Dv50(μm) | Dv90(μm) |
|---|---|---|---|
| Example 38 | 0.769 | 1.992 | 5.336 |

Example 39: Investigation of Stability of Aqueous Suspensions of Cariprazine Embonate and Cariprazine Hydrochloride at 60° C.

The 0-day, 5-day and 10-day particle size and related substances of the cariprazine embonate prepared in Example 33 and the aqueous suspension of cariprazine hydrochloride prepared in Example 38 were measured at 60° C., and the results are shown in the table below.

| Example | Time point | Total impurities (%) | Dv10 (μm) | Dv50 (μm) | Dv90 (μm) |
|---|---|---|---|---|---|
| Example 33 | 0 days | 1.59 | 0.714 | 1.747 | 4.635 |
| | 5 days | 2.21 | 1.045 | 3.345 | 6.428 |
| | 10 days | 2.39 | 1.027 | 3.384 | 6.577 |
| Example 38 | 0 days | 0.45 | 0.769 | 1.992 | 5.336 |
| | 5 days | 1.15 | 49.172 | 98.002 | 201.336 |
| | 10 days | 2.08 | 33.926 | 71.004 | 128.207 |

From the results in the table above, it can be seen that in aqueous suspensions of the same formula, the aqueous suspension of cariprazine embonate was significantly more stable than the aqueous suspension of cariprazine hydrochloride with respect to impurity and particle size.

Examples 40-44: Pharmacokinetic Study of Formula for Cariprazine Embonate Suspension in Rats

| Component | Amount (mg) Example 40 | Example 41 | Example 42 | Example 43 | Example 44 |
|---|---|---|---|---|---|
| Cariprazine embonate in amorphous form (Example 2) | 573 | — | — | — | — |
| Cariprazine embonate in crystalline form A (Example 8) | — | 573 | — | — | 9.5 |
| Cariprazine embonate in crystalline form B (Example 11) | — | — | 573 | — | — |
| Cariprazine embonate in crystalline form E (Example 15) | — | — | — | 573 | — |
| Tween 20 | 100 | 100 | 100 | 100 | 250 |
| Disodium phosphate | 45 | 45 | 45 | 45 | — |
| Monosodium phosphate | 9 | 9 | 9 | 9 | — |
| Mannitol | 247 | 247 | 247 | 247 | — |
| Sodium carboxymethylcellulose | 50 | 50 | 50 | 50 | 175 |
| Water for injection | | | qs 10.0 mL | | Qs 50.0 mL |

1. Process of preparing injectable suspensions of Examples 40-43:

(1) The formula amounts of tween 20, disodium phosphate, monosodium phosphate, mannitol and sodium carboxymethylcellulose were measured out, added to water for injection that was about 60% of the total amount of the preparation, and dissolved and dispersed by stirring.

(2) The formula amounts of corresponding samples of cariprazine embonate were added and completely dispersed by stirring. The mixtures were brought to volume to obtain injectable suspensions of Examples 40-43 having a pH of 7.4±0.2.

(3) The particle size distribution of the samples of Examples 41-43 was measured on an OMEC LS-909 particle size analyzer, and the results are shown in the table below.

| Example | Dv10(μm) | Dv50(μm) | Dv90(μm) |
|---|---|---|---|
| Example 41 | 12.215 | 26.987 | 48.348 |
| Example 42 | 1.842 | 6.713 | 13.673 |
| Example 43 | 0.827 | 2.682 | 6.831 |

2. Process of preparing oral suspension of Example 44:

(1) The formula amounts of tween 20 and sodium carboxymethylcellulose were measured out, added to water for injection that was about 60% of the total amount of the preparation, and dissolved and dispersed by stirring.

(2) The formula amount of cariprazine embonate was added to obtain an aqueous suspension of coarse particles. The pH was adjusted to 5.0 to 5.5 with hydrochloric acid. The suspension was brought to volume to finally obtain the oral suspension of Example 44.

Example 45: Pharmacokinetic Experiment

An in vivo experiment was conducted on rats with the different concentrations of formula samples of cariprazine embonate prepared in Examples 40-44 as follows:

15 male SD rats were divided into five groups, of which four groups were given single doses of formula samples of different crystalline forms of cariprazine embonate by intramuscular injection at 9 mg/kg and plasma was collected 0 h, 1 h, 3 h, 7 h, 24 h, 4 d, 7 d, 11 d, 15 d, 20 d, 25 d and 30 d after administration; the remaining group was orally intragastrically given single doses of the formula sample of crystalline form A of cariprazine embonate at 0.3 mg/kg and plasma was collected min, 15 min, 30 min, 1 h, 2 h, 3 h, 4 h, 6 h, 8 h, 12 h and 24 h after administration. In the whole experiment, the animals from the intramuscular injection group were given ad libitum access to food and water, and those from the oral intragastrical group were fasted overnight before administration and given access to food 4 h after administration.

Plasma sample collection: about 150 μL of blood was collected from the jugular vein (whole blood was centrifuged within 30 min to isolate plasma) and placed in a tube containing anticoagulant EDTA-K2, and after treatment, plasma was stored in a freezer at −70° C. before use.

Pretreatment of plasma sample: to 30 μL of plasma sample was added 200 μL of internal standard solution (40 ng/mL Glipizide acetonitrile solution); the mixture was vortexed for 1 min and centrifuged at 5800 rpm at 4° C. for 10 min; 100 μL of supernatant was transferred to a new plate and 1 μL of solution was taken for LC-MS/MS analysis.

Chromatographic Conditions

Mobile phase composition: mobile phase A: 0.025% formic acid in water-1 mM ammonium acetate mobile phase B: 0.025% methanoic acid in methanol-1 mM ammonium acetate Gradient Elution

| Time (min) | Pump B (%) |
|---|---|
| Initial | 10 |
| 0.20 | 10 |
| 0.70 | 95 |
| 1.30 | 95 |
| 1.31 | 10 |
| 1.80 | 10 |

Chromatography column: Waters ACQUITY UPLC BEH C18 (2.1×50 mm, 1.7 μm);

Flow rate: 0.60 mL/min;

Injection volume: 1 μL;

Column compartment: 60° C.;

Retention time: cariprazine: 1.16 min; Glipizide: 1.22 min.

Mass spectrometry conditions:

Secondary mass spectrometry analysis was performed using an electrospray ion source (Turbo spray) in the multiple reaction monitoring (MRM) mode under the positive ion detection mode. The working parameters and ion source parameters for mass spectrometry analysis are shown in the table below.

| Analyte | Parent ion (m/z) | Daughter ion (m/z) | Dwell time (msec.) | Declustering potential (V) | Collision energy (V) |
|---|---|---|---|---|---|
| Cariprazine | 427.2 | 382.2 | 20 | 80 | 22 |
| Glipizide (IS) | 446.2 | 321.1 | 20 | 77 | 18 |

Figure 22:
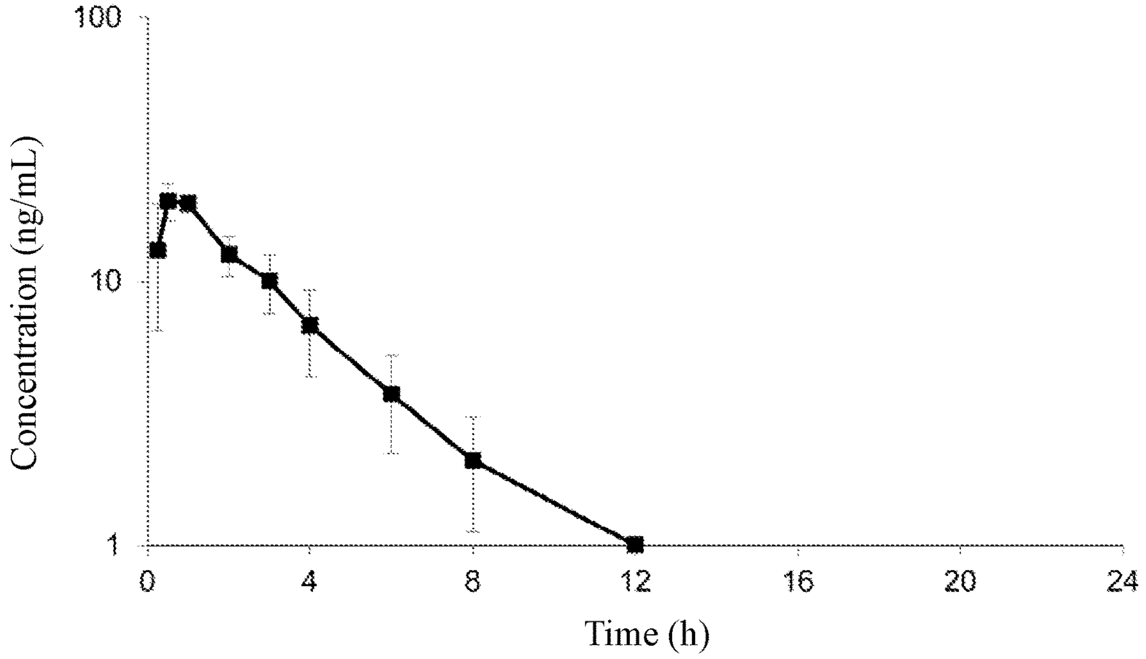
FIG. 22 is a graph showing a relationship between the mean plasma concentration of cariprazine and time in a rat, for an oral sample of the preparation of Example 44 of the present disclosure.
Figure 23:
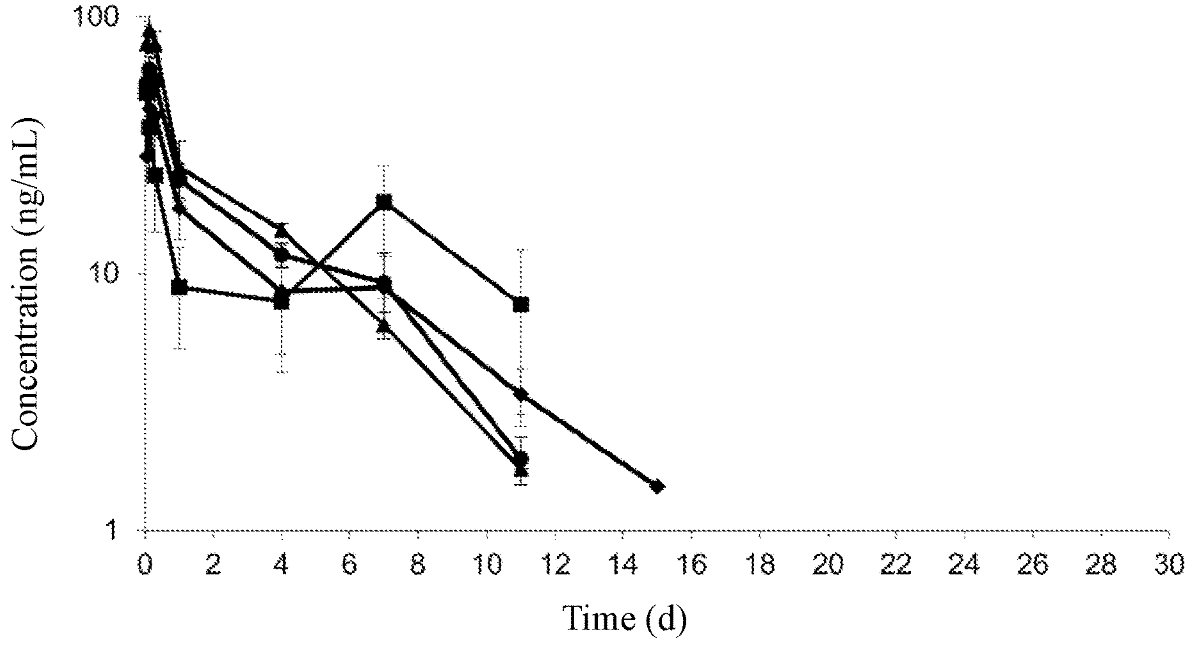
FIG. 23 is a graph showing relationships between the mean plasma concentration of cariprazine and time in rats, for injection samples of the preparations of Examples 40-43 of the present disclosure (■ for amorphous cariprazine embonate; ♦ for crystalline form A of cariprazine embonate; ● for crystalline form B of cariprazine embonate; and ◇ for crystalline form E of cariprazine embonate)
Figure 24:
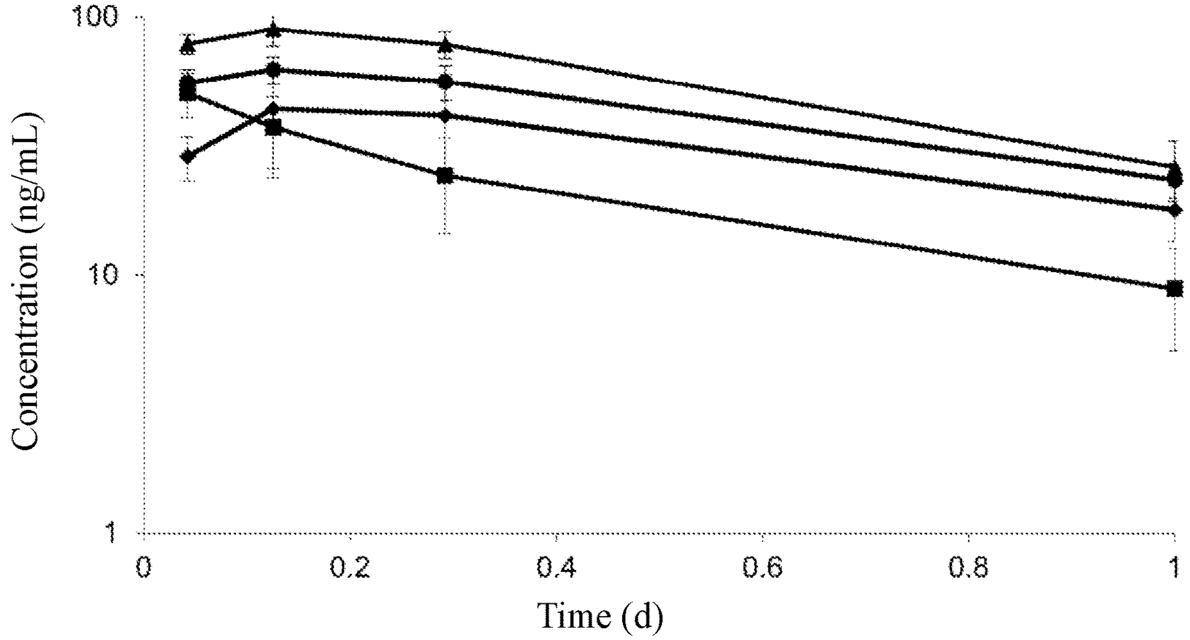
FIG. 24 is a partial, enlarged view of FIG. 23 (showing relationships between the mean plasma concentration of cariprazine and time from 0 to 24 h) (■ for amorphous cariprazine embonate; ♦ for crystalline form A of cariprazine embonate; ● for crystalline form B of cariprazine embonate; and ▲ for crystalline form E of cariprazine embonate).

As can be seen from FIGS. 22-24, the cariprazine embonate oral group achieved fast absorption within 24 h of administering the drug, while the cariprazine embonate injection groups all achieved at least 11 days of sustained release compared to the oral group and, given inter-species differences, are expected to be able to achieve at least 30 days of release in humans. Meanwhile, among the crystalline forms of cariprazine embonate, crystalline form A of cariprazine embonate achieved the best length of release.

From the experimental results of the present disclosure, it can be seen that after the injectable preparations of cariprazine embonate provided by the present disclosure were formulated into aqueous suspensions, cariprazine embonate had relatively small granularity and was evenly distributed, having good injectability and also the characteristic of continuously releasing the drug over a long time (at least one week in SD rats).

The invention claimed is:

1. A pharmaceutical composition of cariprazine, comprising solid particles of cariprazine, wherein the solid particles of cariprazine have a particle size distribution of Dv(10) of ≤30 microns, Dv(50) of ≤50 microns, and Dv(90) of ≤100 microns, and the solid particles of cariprazine are crystalline form A of cariprazine embonate having an X-ray powder diffraction pattern with characteristic peaks at 2θ values of 4.8°±0.2°, 13.1°±0.2°, 18.7°±0.2°, 20.1°±0.2°, 21.0°±0.2°, and 26.1°±0.2°.

2. The pharmaceutical composition of cariprazine as claimed in claim 1, wherein:

the X-ray powder diffraction pattern of the crystalline form A of cariprazine embonate has characteristic peaks at 2θ values of 4.8°±0.2°, 9.7±0.2°, 12.3°±0.2°, 13.1°±0.2°, 18.7°±0.2°, 20.1°±0.2°, 21.0°±0.2°, and 26.1°±0.2°.

3. The pharmaceutical composition of cariprazine as claimed in claim 1, wherein the composition is an injectable preparation that comprises one or more selected from a suspending agent, a wetting agent, an osmotic pressure regulator, a solvent, a stabilizer, a buffer, and a surfactant.

4. The pharmaceutical composition of cariprazine as claimed in claim 3, wherein the suspending agent is at a concentration in the range of 0 mg/mL to 10 mg/mL;

and/or, the suspending agent is one or more selected from sodium carboxymethylcellulose, methylcellulose, and polyvinylpyrrolidone.

5. The pharmaceutical composition of cariprazine as claimed in claim 3, wherein the wetting agent is at a concentration in the range of 1 mg/mL to 10 mg/ml;

and/or, the wetting agent is one or more selected from polysorbate 20, polysorbate 80, and poloxamer 188.

6. The pharmaceutical composition of cariprazine as claimed in claim 3, wherein: the osmotic pressure regulator is at a concentration in the range of 20 mg/mL to 30 mg/mL;

and/or, the osmotic pressure regulator is selected from one or more of sodium chloride, mannitol and sucrose;

and/or, the stabilizer is at a concentration in the range of 0 mg/mL to 30 mg/mL;

and/or, the stabilizer is PVP K12;

and/or, the buffer is selected from one or more of phosphoric acid, phosphate, citric acid, sodium citrate, hydrochloric acid and sodium hydroxide;

and/or, the surfactant is sodium deoxycholate;

and/or, the solvent is water for injection.

7. The pharmaceutical composition of cariprazine as claimed in claim 3, wherein the composition comprises:

cariprazine embonate, sodium carboxymethylcellulose, polysorbate20, disodium phosphate, monosodium phosphate, mannitol, and, optionally, sodium hydroxide or hydrochloric acid.

8. The pharmaceutical composition of cariprazine as claimed in claim 7, wherein the solid particles of cariprazine embonate are at a concentration of no less than 15 mg/mL.

9. A preparation method for the pharmaceutical composition of cariprazine as claimed in claim 3, comprising the following steps:

sequentially dissolving the wetting agent, the buffering agent and the osmotic pressure regulator in water for injection to obtain a mixture;

adding the solid particles of cariprazine embonate to the mixture to obtain an aqueous suspension of coarse particles;

grinding the aqueous suspension of coarse particles to obtain a suspension; and adding the suspending agent to the suspension, adjusting pH of the suspension to 4.0-9.0 with sodium hydroxide or hydrochloric acid, and bringing the suspension to a predetermined volume to obtain the injectable preparation.

10. A method for treating psychosis, bipolar disorder and/or acute mania, comprising administering the pharmaceutical composition of cariprazine as claimed in claim 1 to a patient in need thereof.

11. The pharmaceutical composition of cariprazine as claimed in claim 1, wherein Dv(90) of the solid particles ranges from 10 microns to 100 microns.

12. The pharmaceutical composition of cariprazine as claimed in claim 4, wherein the suspending agent is at a concentration in the range of 3.5 mg/mL to 5 mg/ml;

and/or, the suspending agent is carboxymethylcellulose.

13. The pharmaceutical composition of cariprazine as claimed in claim 5, wherein the wetting agent is at a concentration in the range of 1 mg/mL to 5 mg/mL;

and/or, the wetting agent is polysorbate 20.

14. The pharmaceutical composition of cariprazine as claimed in claim 5, wherein the osmotic pressure regulator is at a concentration in the range of 23 mg/mL to 26 mg/mL;

and/or, the stabilizer is at a concentration in the range of 1 mg/mL to 10 mg/mL.

15. The pharmaceutical composition of cariprazine as claimed in claim 1, wherein the solid particles of cariprazine have a particle size distribution of Dv(10) of 9.338 microns, Dv(50) of 27.446 microns and Dv(90) of 79.618 microns; or, Dv(10) of 1.257 microns, Dv(50) of 4.794 microns and Dv(90) of 14.601 microns; or, Dv(10) of 12.215 microns, Dv(50) of 26.987 microns and Dv(90) of 48.348 microns.

* * * * *